US009803251B2

(12) United States Patent
Tong

(10) Patent No.: US 9,803,251 B2
(45) Date of Patent: Oct. 31, 2017

(54) METHODS OF DETECTING INFLUENZA VIRUS

(71) Applicant: The United States of America as represented by the Secretary of the Department of Health and Human Services, Washington, DC (US)

(72) Inventor: Suxiang Tong, Duluth, GA (US)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 154 days.

(21) Appl. No.: 14/398,383

(22) PCT Filed: Mar. 7, 2013

(86) PCT No.: PCT/US2013/029600
§ 371 (c)(1),
(2) Date: Oct. 31, 2014

(87) PCT Pub. No.: WO2013/165551
PCT Pub. Date: Nov. 7, 2013

(65) Prior Publication Data
US 2015/0133329 A1 May 14, 2015

Related U.S. Application Data

(60) Provisional application No. 61/642,098, filed on May 3, 2015.

(51) Int. Cl.
C12Q 1/70 (2006.01)
(52) U.S. Cl.
CPC ....... *C12Q 1/701* (2013.01); *C12Q 2600/158* (2013.01)
(58) Field of Classification Search
CPC .......................... C12Q 1/701; C12Q 2600/158
USPC ..... 424/91.1, 91.2, 91.23; 436/63; 536/23.1, 536/23.72
See application file for complete search history.

(56) References Cited

U.S. PATENT DOCUMENTS

| | | | | |
|---|---|---|---|---|
| 2007/0087336 A1* | 4/2007 | Sampath | ................ | C12Q 1/701 435/5 |
| 2007/0231348 A1* | 10/2007 | Kawaoka | ............. | A61K 39/145 424/209.1 |
| 2009/0010962 A1* | 1/2009 | Palese | .................. | A61K 39/145 424/199.1 |
| 2009/0047286 A1* | 2/2009 | Gramer | ................ | C07K 14/005 424/139.1 |
| 2009/0088331 A1 | 4/2009 | Wu et al. | | |
| 2010/0248219 A1* | 9/2010 | Sampath | ................ | C12Q 1/701 435/6.16 |
| 2012/0191364 A1* | 7/2012 | Wong | ...................... | G06F 19/20 702/19 |
| 2013/0267429 A1* | 10/2013 | Gardner | .................. | G06F 19/20 506/8 |

OTHER PUBLICATIONS

Fouchier et al, J. Clin. Microbiol. 38(11):4096-4101, 2000.*
Lee et al, J. Virol. Methods 165:133-138, 2010.*
Muscle, EMBL-EBI Multiple Sequence Alignment, Kawaoka SEQ ID Nos. 10 and 28; alignments created Oct. 11, 2016.*
Muscle, EMBL-EBI Multiple Sequence Alignment, Sampathe Sampath SEQ ID Nos. 75, 76, 78, 81, 82 and 125; alignments created Oct. 11, 2016.*
EBI Database Accession No. ATT04782, Jan. 22, 2009, 2 pages.
EBI Database Accession No. AYJ81289, Nov. 25, 2010, 1 page.
EBI Database Accession No. AYJ81323, Nov. 25, 2010, 1 page.
Fouchier et al., "Characterization of a Novel Influenza A Virus Hemagglutinin Subtype (H16) Obtained from Black-Headed Gulls," *Journal of Virology*, vol. 79, No. 5, pp. 2814-2822, 2005.
Fouchier et al., "Detection of Influenza A Viruses from Different Species by PCR Amplification of Conserved Sequences in the Matrix Gene," *Journal of Clinical Microbiology*, Vo. 38, No. 11, pp. 4096-4101, 2000.
Huber et al., "A multiplex one-step real-time PCR assay for influenza surveillance," *Euro. Surveill.*, 16(7):pii=19798, 2011 (7 pages).
Lee et al., "Genotyping and screening of reassortant live-attenuated influenza B vaccine strain," *Journal of Virological Methods*, vol. 165, No. 2, pp. 133-138, 2010.
Spackman et al., "Type A Influenza Virus Detection and Quantitation by Real-Time RT-PCR," *Methods in Molecular Biology*, vol. 436, pp. 19-26, 2008.
Tong et al., "Sensitive and Broadly Reactive Reverse Transcription-PCR Assays to Detect Novel Paramyxoviruses," *Journal of Clinical Microbiology*, vol. 46, No. 8, 2652-2658, 2008.
Tong et al., "A distinct lineage of influenza A virus from bats," PNAS, vol. 109, No. 11, pp. 4269-4274, 2012 (including supplemental material, 53 pages).

* cited by examiner

*Primary Examiner* — Kevin Hill
(74) *Attorney, Agent, or Firm* — Klarquist Sparkman, LLP

(57) ABSTRACT

Disclosed herein are methods of detecting influenza virus in a sample from a subject. In some embodiments, the disclosed methods include contacting a sample with at least one primer 10-40 nucleotides in length wherein the at least one primer is capable of hybridizing to an influenza virus polymerase basic protein 1 (PB1) nucleic acid at least 70% identical to the nucleic acid sequence set forth as any one of SEQ ID NOs: 1-3, amplifying the PB1 nucleic acid or a portion thereof to produce an amplified PB1 nucleic acid, and detecting the amplified PB1 nucleic acid, wherein presence of the amplified PB1 nucleic acid indicates presence of influenza virus in the sample from the subject. In some examples, the primers comprise or consist of the nucleic acid sequence set forth as one of SEQ ID NO: 4, SEQ ID NO: 5, SEQ ID NO: 9, or SEQ ID NO: 10.

7 Claims, 12 Drawing Sheets

| | | Group 1 | | | | | | | | | | | | Group 2 | | | | | | | |
|---|---|---|---|---|---|---|---|---|---|---|---|---|---|---|---|---|---|---|---|---|---|
| HA | A/bat/Peru/10/118 IIA | H1 | H2 | H5 | H6 | H17 | H11 | H13 | H16 | H8 | H9 | H12 | Average Group 1 | H3 | H4 | H14 | H7 | H10 | H15 | Average Group 2 | All HAs (average) |
| Group 1 | | | | | | | | | | | | | | | | | | | | | |
| H1 | 50.2 | 65.0 | | | | | | | | | | | | | | | | | | | |
| H2 | 52.9 | 63.0 | 75.9 | | | | | | | | | | | | | | | | | | |
| H5 | 54.5 | 59.1 | 58.5 | 60.4 | | | | | | | | | | | | | | | | | |
| H6 | 50.0 | 51.8 | 54.4 | 53.6 | 52.3 | | | | | | | | | | | | | | | | |
| H17 | 60.2 | 53.9 | 54.7 | 57.0 | 55.0 | 46.5 | | | | | | | | | | | | | | | |
| H11 | 46.0 | 50.2 | 50.3 | 51.2 | 51.2 | 45.6 | 59.1 | | | | | | | | | | | | | | |
| H13 | 45.5 | 51.2 | 49.8 | 50.8 | 48.7 | 45.2 | 59.3 | 81.6 | | | | | | | | | | | | | |
| H16 | 45.0 | 51.0 | 48.5 | 50.3 | 53.7 | 48.3 | 48.9 | 48.1 | 49.5 | | | | | | | | | | | | |
| H8 | 46.1 | 50.9 | 51.6 | 50.8 | 54.5 | 48.4 | 52.4 | 51.2 | 49.6 | 62.5 | | | | | | | | | | | |
| H9 | 46.0 | 50.9 | 48.9 | 48.8 | 51.2 | 45.5 | 48.9 | 49.3 | 49.6 | 64.3 | 65.3 | | | | | | | | | | |
| H12 | 43.8 | 47.4 | 48.9 | 48.8 | 51.2 | 45.5 | 48.9 | 49.3 | 49.6 | 64.3 | 65.3 | | | | | | | | | | |
| Average Group 1 | 49.1 | | | | | | | | | | | | 53.5 | | | | | | | | |
| Group 2 | | | | | | | | | | | | | | | | | | | | | |
| H3 | 36.3 | 42.1 | 41.4 | 42.5 | 42.0 | 36.6 | 39.6 | 37.7 | 37.9 | 41.4 | 40.7 | 40.3 | | 64.1 | | | | | | | |
| H4 | 37.6 | 42.3 | 42.5 | 41.8 | 42.2 | 37.3 | 41.2 | 40.8 | 40.4 | 44.6 | 43.2 | 42.5 | | 64.8 | 77.9 | | | | | | |
| H14 | 38.1 | 42.6 | 42.0 | 43.1 | 43.2 | 38.9 | 41.4 | 43.3 | 41.9 | 43.3 | 42.6 | 41.1 | | 46.9 | 47.2 | 48.1 | | | | | |
| H7 | 39.5 | 43.2 | 41.5 | 42.2 | 41.7 | 38.3 | 41.1 | 39.4 | 38.4 | 40.0 | 39.3 | 41.0 | | 49.5 | 50.0 | 49.6 | 61.8 | | | | |
| H10 | 37.5 | 44.1 | 42.9 | 42.1 | 42.9 | 36.8 | 42.7 | 41.0 | 40.0 | 41.8 | 41.2 | 40.8 | | 47.1 | 48.2 | 49.7 | 80.0 | 65.2 | | | |
| H15 | 40.1 | 43.4 | 41.4 | 40.9 | 42.3 | 37.5 | 41.9 | 40.0 | 38.6 | 40.4 | 39.7 | 40.9 | | | | | | | | | |
| Average Group 2 | 38.2 | | | | | | | | | | | | | | | | | | | 56.7 | |
| All HAs (average) | 45.3 | | | | | | | | | | | | | | | | | | | | 47.8 |

FIG. 6

| NA subtype | A/bat/Peru/10 N11 | N1 | N2 | N3 | N4 | N5 | N6 | N7 | N8 | N9 | N10 |
|---|---|---|---|---|---|---|---|---|---|---|---|
| N1 | 31.0 | | | | | | | | | | |
| N2 | 25.0 | 45.2 | | | | | | | | | |
| N3 | 23.6 | 46.2 | 51.6 | | | | | | | | |
| N4 | 31.3 | 69.7 | 45.5 | 46.5 | | | | | | | |
| N5 | 31.6 | 59.2 | 43.9 | 42.0 | 47.3 | | | | | | |
| N6 | 26.1 | 46.2 | 49.5 | 47.9 | 43.6 | 46.8 | | | | | |
| N7 | 26.8 | 44.5 | 47.3 | 45.8 | 42.5 | 44.2 | 59.7 | | | | |
| N8 | 32.4 | 56.8 | 46.8 | 43.5 | 59.2 | 72.2 | 47.1 | 43.4 | | | |
| N9 | 26.4 | 42.0 | 48.7 | 47.1 | 40.9 | 40.5 | 68.4 | 60.6 | 41.9 | | |
| N10 | 42.0 | 27.8 | 23.6 | 26.8 | 28.7 | 28.5 | 22.6 | 26.6 | 27.0 | 22.3 | |
| Average Flu A | 29.6 | 33.6 | 30.4 | 30.9 | 33.6 | 34.5 | 31.7 | 31.5 | 34.0 | 32.1 | 23.7 |
| Flu B | 26.3 | | | | | 44.6 | | | | | |
| Average Flu B | | | | | | 31.6 | | | | | |

METHODS OF DETECTING INFLUENZA VIRUS

CROSS REFERENCE TO RELATED APPLICATIONS

This is the §371 U.S. National Stage of International Application No. PCT/US2013/029600, filed Mar. 7, 2013, which was published in English under PCT Article 21(2), which in turn claims the benefit of U.S. Provisional Application No. 61/642,098, filed May 3, 2012, which is incorporated herein by reference in its entirety.

FIELD

This disclosure relates to methods and compositions for the detection of influenza virus in a sample or a subject.

BACKGROUND

Emerging infectious diseases and pandemics in humans often originate from pathogens transmitted from nonhuman animal reservoirs. The pandemics of severe acute respiratory syndrome, HIV, and 2009 H1N1 influenza illustrate the dramatic impact of viral host-switching on public health and the global economy. Early prediction, detection, characterization, and risk assessment of viruses in their animal hosts, before they spread into the human population, are critical to protect public health.

Most influenza A viruses circulate in waterfowl, but those that infect mammalian hosts are thought to pose the greatest risk for zoonotic spread to humans and the generation of pandemic or panzootic viruses. Bats (order Chiroptera) are of particular interest, because they comprise nearly 1,200 species worldwide, accounting for approximately one-fourth of all mammalian species, and their global distribution, abundance, ability to fly and migrate over large distances, and sociality favors the acquisition and spread of viruses. In recent history, bats have been sources of multiple pathogenic viruses for humans and domestic animals, including coronaviruses, filoviruses, henipaviruses, and lyssaviruses. Pathogen-specific assays which are commonly used in the laboratory however, are not always sufficient to determine the etiology of cases or outbreaks of viral disease. Thus, there is a need to detect previously known as well as novel influenza viruses and influenza-related viruses in human and animal populations.

SUMMARY

Disclosed herein are compositions and methods for detecting influenza virus in a sample. The disclosed methods and primers are capable of detecting any type of influenza virus (such as influenza A virus, influenza B virus, and/or influenza C virus) in a sample, including novel or previously unknown influenza viruses or influenza-related viruses. Such methods and compositions are useful for diagnosing a subject with influenza virus infection, discovery of novel influenza viruses, and early detection and monitoring of zoonotic viruses, among others.

In some embodiments, the disclosed methods include amplifying from a sample an influenza virus polymerase basic protein 1 (PB1) nucleic acid that is at least 70% identical (for example at least 75%, 80%, 85%, 90%, 95%, or more identical) to the nucleic acid sequence set forth as any one of SEQ ID NOs: 1-3 or a portion thereof, and detecting the amplified PB1 nucleic acid. In some examples, the method includes contacting a sample with at least one primer 10-40 nucleotides in length, wherein the at least one primer is capable of hybridizing to an influenza virus PB1 nucleic acid that is at least 70% identical to the nucleic acid sequence set forth as any one of SEQ ID NOs: 1-3, amplifying the PB1 nucleic acid to produce an amplified PB1 nucleic acid, and detecting the amplified PB1 nucleic acid, wherein presence of the amplified PB1 nucleic acid indicates presence of an influenza virus in the sample from the subject. In some examples, the at least one primer comprises or consists of the nucleic acid sequence set forth as SEQ ID NO: 4, SEQ ID NO: 5, SEQ ID NO: 9, or SEQ ID NO: 10.

The foregoing and other features of the disclosure will become more apparent from the following detailed description, which proceeds with reference to the accompanying figures.

BRIEF DESCRIPTION OF THE DRAWINGS

FIG. 1A), neuraminidase (NA; FIG. 1B), polymerase basic protein 2 (PB2; FIG. 1C), polymerase basic protein 1 (PB1; FIG. 1D), polymerase (PA, FIG. 1E), nucleoprotein (NP, FIG. 1F), matrix (M, FIG. 1G), and nonstructural (NS, FIG. 1H) gene segments.

FIG. 5 shows the mean amino acid identity between A/bat/Peru/10 H18 HA and influenza A subtypes H1-H17.

FIG. 6 shows the mean amino acid identity between the A/bat/Peru/10 N11 NAL and representative NAs of influenza A and B viruses.

SEQUENCE LISTING

Figure 1A:
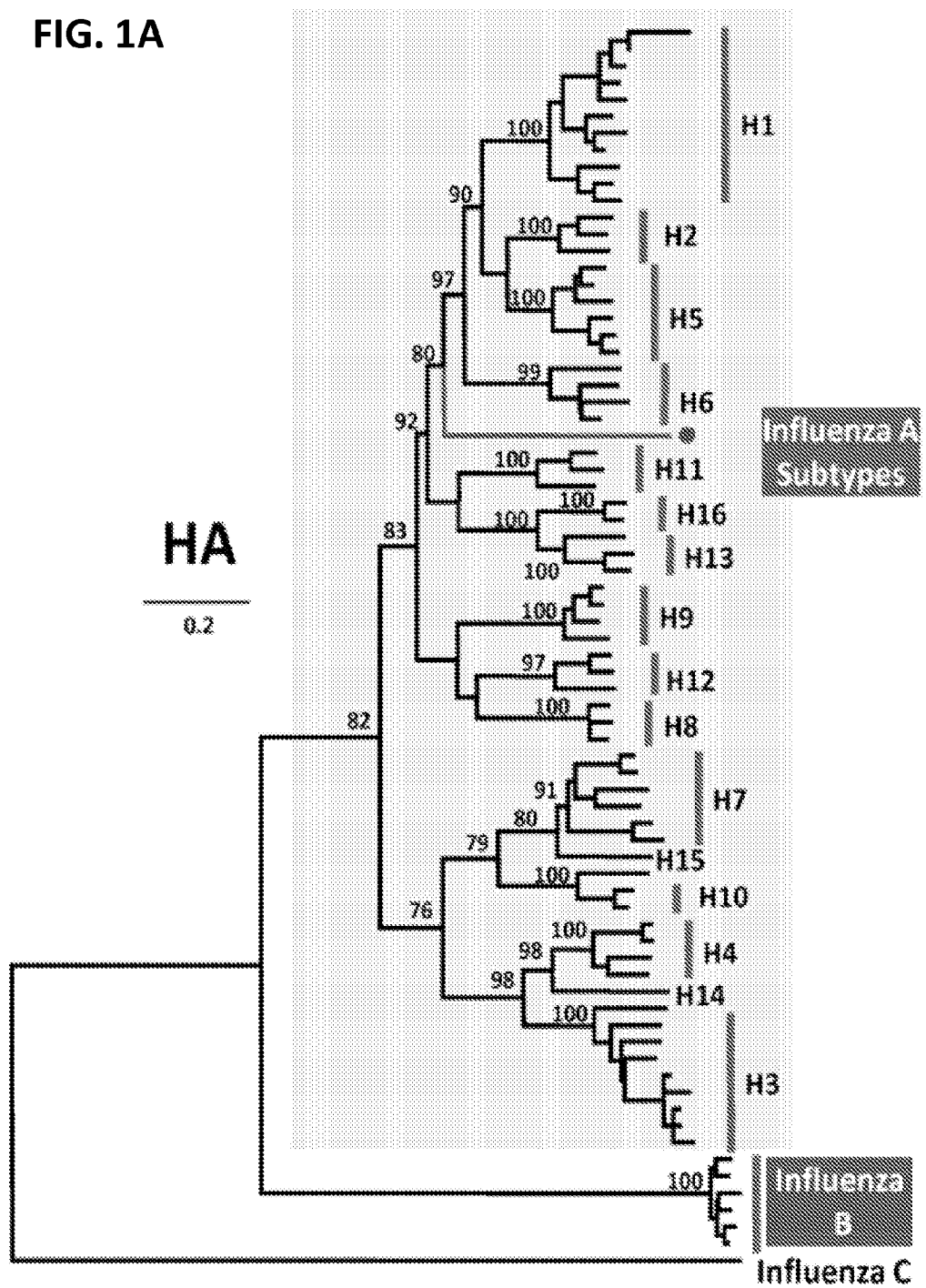
FIGS. 1A-H are a series of phylogenetic trees of the eight gene segments of sequenced bat influenza virus genomes (represented by the dot) inferred by the maximum-likelihood method. Bootstrap values are shown above branches to the left of major nodes denoting influenza A, influenza B and A/bat/Guat/09 divergences. Trees are shown for hemagglutinin (HA.

Any nucleic acid and amino acid sequences listed herein or in the accompanying sequence listing are shown using standard letter abbreviations for nucleotide bases, and three letter code for amino acids, as defined in 37 C.F.R. §1.822.

In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 30, 2014, and is 12,023 bytes, which is incorporated by reference herein.

SEQ ID NO: 1 is an exemplary nucleic acid sequence of an influenza A virus PB1 gene.

SEQ ID NO: 2 is an exemplary nucleic acid sequence of an influenza B virus PB1 gene.

SEQ ID NO: 3 is an exemplary nucleic acid sequence of an influenza C virus PB1 gene.

SEQ ID NOs: 4 and 5 are nucleic acid sequences of pan-influenza Flu-Pan-F3 and Flu-Pan-R4-2 forward and reverse PCR primers, respectively.

SEQ ID NOs: 6-8 are nucleic acid sequences of GTM Flu NP primers and probe.

SEQ ID NOs: 9 and 10 are nucleic acid sequences of pan-influenza Flu-Pan-F2-2 and Flu-Pan-R3-3 forward and reverse PCR primers, respectively.

DETAILED DESCRIPTION

Wild populations of waterfowl are considered hosts to the most diverse influenza A viruses, including 16 distinct alleles of the HA gene and nine alleles of the NA gene. Sporadically, these viruses infect mammals, and in rare instances these events lead to sustained transmission in the new mammalian host. Human, swine, and equine influenza viruses are thought to have emerged directly or indirectly from this avian reservoir. The influenza viruses of domesticated animals, particularly those of swine, are thought to pose the greatest risk for zoonotic spread to humans and the generation of pandemic or panzootic viruses.

Using the methods and primers disclosed herein, the inventor has demonstrated that new world bats in Central and South America also are hosts of novel influenza A viruses and constitute a potential sylvatic mammalian reservoir of influenza. These novel viruses are significantly divergent from known influenza A viruses, such that their HA and NA can be classified as separate subtypes.

The disclosed methods and compositions are advantageous in that they can detect the presence of any known type of influenza virus (for example, influenza A, influenza B and/or influenza C) in a sample and is referred to herein as "pan-flu" or "pan-influenza" virus detection. In contrast, previously described methods have focused on pan-influenza virus A, pan-influenza virus B, or pan-influenza virus C detection; that is, the methods could detect any influenza A virus (but not necessarily an influenza B or C virus), any influenza B virus (but not necessarily an influenza A or C virus), or any influenza C virus (but not necessarily an influenza A or B virus). The disclosed methods have been validated with high sensitivity (detection of about 100-500 copies) and specificity, using representatives of all known subtypes of influenza A, B, and C species.

In addition to being useful for identifying presence of influenza virus in a sample in a single assay (regardless of whether the type is known), the disclosed methods and primers can be used to detect presence of a novel influenza virus or influenza-related virus in a sample. This can provide detection and monitoring of emerging novel influenza viruses with the potential for spreading to human populations.

I. Abbreviations
  HA hemagglutinin
  I inosine
  M matrix
  N degenerate nucleotide position
  NA neuraminidase
  NP nucleoprotein
  NS nonstructural
  PA polymerase
  PB1 polymerase basic protein 1
  PB2 polymerase basic protein 2
  RT-PCR reverse transcriptase-polymerase chain reaction
  TNA total nucleic acids II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. As used herein, "comprises" means "includes." Thus, "comprising A or B," means "including A, B, or A and B," without excluding additional elements. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include real-time PCR; quantitative real-time PCR; reverse transcriptase PCR (RT-PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see Eur. Pat. Publ. EP320308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025, 134); amongst others. Additional amplification techniques include cell cloning and cell-based DNA cloning (see Strachan and Read, *Human Molecular Genetics,* 2$^{nd}$ edition, Wiley-Liss, 1999).

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as an influenza virus nucleic acid. For example, a probe or primer (such as SEQ ID NOs: 4, 5, 9, or 10) having some homology to a disclosed influenza virus nucleic acid molecule will form a hybridization complex with a complementary nucleic acid molecule (such as any of SEQ ID NOs: 1-3). If a primer is used, the influenza virus nucleic acid can be amplified, for example using PCR.

Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular Cloning,* second edition, Cold Spring Harbor Laboratory, Plainview, N.Y. (chapters 9 and 11). The following is an exemplary set of hybridization conditions and is not limiting:

Very High Stringency (Detects Sequences That Share At Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences That Share At Least 80% Identity)
Hybridization: 5x-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2x-3×SSC at RT to 55° C. for 20-30 minutes each.

The probes and primers disclosed herein can hybridize to nucleic acid molecules under low stringency, high stringency, or very high stringency conditions.

Influenza Virus: A segmented negative-strand RNA virus that belongs to the Orthomyxoviridae family. There are three types of Influenza viruses, A, B and C. Influenza A viruses infect a wide variety of birds and mammals, including humans, horses, marine mammals, water fowl, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. H5N1 is also referred to as "avian influenza." Influenza A viruses can be further classified into subtypes based on allelic variations in antigenic regions of two genes that encode surface glycoproteins, namely, hemagglutinin (HA) and neuraminidase (NA) which are required for viral attachment and cellular release. The host range of influenza B virus is significantly more limited, with only humans, seals, and ferrets known to be susceptible to influenza B. Influenza C virus infects humans, dogs, and pigs and generally causes mild illness.

Pan-Influenza Detection: Detection of any type or subtype of influenza virus or a closely related virus (for example in a sample from a subject or in an environmental sample) in a single assay or reaction. Pan-influenza detection can include detecting one or more of influenza A virus, influenza B virus, influenza C virus, or a combination of two or more thereof in a sample in a single reaction, for example with a single set of primers and/or probes. In some embodiments, pan-influenza detection indicates the presence of an influenza virus or closely related virus in a sample, without identifying the particular type or subtype of influenza virus (or related virus).

Polymerase Basic Protein 1 (PB1): PB1 is the catalytic subunit of RNA-dependent RNA polymerase of influenza viruses. The influenza virus RNA polymerase includes three subunits (PB1, PB2, and PA). PB1 is the core subunit, including catalytic activity and assembly of PB2 and PA into the fully functional enzyme complex.

Influenza virus PB1 nucleic acid and protein sequences are publicly available. Exemplary PB1 nucleic acid sequences include GenBank Accession Nos. JQ689090 and NC_002021 (influenza A virus), M14880 and NC_002204 (influenza B virus), and FR671421 and NC_006308 (influenza C virus), each of which are incorporated herein by reference as present in GenBank on Apr. 24, 2012. One of ordinary skill in the art can identify additional PB1 sequences, for example using Blast (available on the World Wide Web at blast.ncbi.nlm.nih.gov/Blast).

Primers: Short nucleic acid molecules, for instance DNA oligonucleotides 10-100 nucleotides in length, such as about 10, 15, 20, 25, 30, 40, 45, or 50 nucleotides or more in length. Primers can be annealed to a complementary target DNA strand by nucleic acid hybridization to form a hybrid between the primer and the target DNA strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under low, high, and/or very high stringency hybridization conditions. Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence.

In particular examples, a primer is at least 10 nucleotides in length, such as at least 10 contiguous nucleotides complementary to a target nucleic acid molecule. Particular lengths of primers that can be used to practice the methods of the present disclosure include primers having at least 10, such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more contiguous nucleotides complementary to the target nucleic acid molecule to be amplified, such as a primer of 10-60 nucleotides, 15-50 nucleotides, 20-40 nucleotides, 25-50, nucleotides, or 10-40 nucleotides.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 10, at least 15, at least 20, at least 25, at least 30, at least 35, at least 40, at least 45, at least 50 or more consecutive nucleotides of a target sequence.

Sample: Refers to any biological or environmental sample. In some embodiments, the sample is a biological sample obtained from a subject, such as a mucous, saliva, blood, urine, or fecal sample. In other embodiments, the sample is an environmental sample, such as a liquid sample (for example, water or sewage) or a soil sample.

Sequence Identity/Similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, available on the world wide web at ncbi.nlm.nih.gov), for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid primers disclosed herein are not limited to the exact sequences shown, as those of ordinary skill in the art will appreciate that changes can be made to a sequence, and not substantially affect the ability of a primer to function as desired. For example, sequences having at least 70%, at least 75%, at least 80%, at least 85%, at least 90%, at least 95% or more sequence identity to SEQ ID NO: 4, SEQ ID NO: 5, SEQ ID NO: 9, or SEQ ID NO: 10 are provided herein. One of ordinary skill in the art will appreciate that these sequence identity ranges are provided for guidance only; it is possible that primers can be used that fall outside these ranges.

Subject: Living multi-cellular vertebrate organisms, a category that includes both human and non-human mammals (such as dogs, swine, and bats) and birds (such as poultry and water fowl). In some embodiments herein, the subject is a human.

III. Methods for Detecting Influenza Virus in a Sample

Methods for detecting the presence of a known or novel influenza virus (such as a virus belonging to the genera Influenzavirus A, Influenzavirus B, or Influenzavirus C) or a related virus (such as a member of the family Orthomyxoviridae) in a sample are disclosed, for example, utilizing the primers disclosed herein. The methods described herein may be used for any purpose for which detection of influenza virus is desirable, including diagnostic and prognostic applications, such as in laboratory and clinical settings. Additional uses include, but are not limited to, discovery of novel influenza viruses, and early detection and monitoring of zoonotic viruses.

In some embodiments, the disclosed methods include amplifying from a sample an RNA-dependent RNA polymerase basic protein 1 (PB1) nucleic acid, such as a nucleic acid sequence set forth as one of SEQ ID NOs: 1-3 (or a portion thereof) or a sequence having at least 70% sequence identity to one of SEQ ID NOs: 1-3 (or a portion thereof) and detecting the amplified PB1 nucleic acid. One of ordinary skill in the art can select appropriate amplification methods. In some examples, the PB1 nucleic acid is amplified with a primer that is capable of hybridizing (for example under low, high, or very high stringency conditions) to the nucleic acid sequence set forth as one of SEQ ID NOs: 1-3 or a sequence having at least 70% sequence identity to one of SEQ ID NOs: 1-3. In some embodiments, the nucleic acids detected using the methods provided herein include nucleic acid molecules from influenza virus. In some examples, influenza viruses include influenza A virus (for example, H1-H18 subtypes), influenza B virus (for example, Yamagata and Victoria lineages), and influenza C virus. Viral strains may be obtained from patient, animal, or environmental samples or viral collections, for example, the American Type Culture Collection (Manassas, Va.).

Appropriate samples include any conventional biological or environmental sample, including clinical samples obtained from a human or animal subject. Suitable samples include all biological samples useful for detection of viral infection in subjects, including, but not limited to, cells, tissues (for example, lung, liver, and kidney), autopsy samples, bodily fluids (for example, blood, serum, urine, cerebrospinal fluid, middle ear fluids, bronchoalveolar lavage, tracheal aspirates, sputum, nasopharyngeal swabs or aspirates, oropharyngeal swabs or aspirates, or saliva), eye swabs, cervical swabs, vaginal swabs, rectal swabs, cloacal swabs, stool, and fecal samples. In some examples, the subject is a human subject. In other examples, the subject is an animal subject, such as an animal known or suspected to be a reservoir for influenza virus. In some examples, animal reservoirs for influenza virus include wild or domestic animals, such as pigs, poultry (for example, chickens or turkeys), waterfowl (for example, ducks or geese), bats, dogs, horses, ferrets, and marine mammals (for example, seals).

One of ordinary skill in the art will know suitable methods for extracting nucleic acids such as RNA and/or DNA from a sample; such methods will depend upon, for example, the type of sample in which the influenza virus nucleic acid is found. Nucleic acids can be extracted using standard methods. For instance, rapid nucleic acid preparation can be performed using a commercially available kit (such as kits and/or instruments from Qiagen (such as DNEASY®, RNEASY®, or QIAAMP® kits), Roche Applied Science (such as MAGNA® Pure kits and instruments), Thermo Scientific (KingFisher mL), bioMerieux (NUCLISENS® NASBA Diagnostics), or Epicentre (MASTERPURE™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162: 156-159, 1987). The sample can be used directly or can be processed, such as by adding solvents, preservatives, buffers, or other compounds or substances.

In some examples, the disclosed methods include amplifying a PB1 nucleic acid at least 70% identical (for example at least 75%, at least 80%, at least 85%, at least 90%, at least 95%, at least 96%, at least 97%, at least 98%, at least 99%, or 100% identical) to the nucleic acid sequence set forth as any one of SEQ ID NOs: 1-3 or a portion thereof from a sample and detecting the amplified PB1 nucleic acid. Any method of nucleic acid amplification can be utilized. One of ordinary skill in the art can select an appropriate method of amplification. In particular examples, the methods include contacting the sample with at least one primer between 10 and 40 nucleotides in length, wherein the at least one primer is capable of hybridizing under low, high, or very high stringency conditions to an influenza virus polymerase basic protein 1 (PB1) nucleic acid at least 70% identical (for example at least 75%, at least 80%, at least 85%, at least 90%, at least 95%, at least 96%, at least 97%, at least 98%, at least 99%, or 100% identical) to the nucleic acid sequence set forth as any one of SEQ ID NOs: 1-3, amplifying the PB1 nucleic acid or a portion thereof to produce an amplified PB1 nucleic acid, and detecting the amplified PB1 nucleic acid, wherein presence of the amplified PB1 nucleic acid indicates presence of influenza virus in the sample from the subject.

In some examples, the at least one primer is capable of hybridizing under high stringency or very high stringency conditions to a nucleic acid molecule including or consisting of one or more of SEQ ID NOs: 1-3. One of ordinary skill in the art can determine low, high, or very high stringency conditions for hybridization of a primer or probe (such as a primer disclosed herein) to a nucleic acid sequence (such as a sequence with at least 70% identity to one of SEQ ID NOs: 1-3). In some examples, the conditions are for hybridization of a primer or probe to a nucleic acid attached to a solid support (such as the conditions provided above). In other examples, the conditions are for hybridization of a primer or probe to a nucleic acid in solution, such as a PCR reaction mixture. In some examples, non-limiting examples, low stringency conditions include hybridization (such as an annealing step in PCR) at a temperature of about 45-50° C. In other examples, high stringency conditions include hybridization (such as an annealing step in PCR) at a temperature of about 50-60° C. In further examples, very high stringency conditions include hybridization (such as an annealing step in PCR) at a temperature of greater than 60° C. One of ordinary skill in the art can determine appropriate hybridization or annealing conditions (including the degree of hybridization) based on the particular primers or probes and target nucleic acids to be amplified or detected.

A region of an influenza virus PB1 nucleic acid that is at least about 50, at least about 60, at least about 70, at least about 80, at least about 90, at least about 100, at least about 110, at least about 120, at least about 130, at least about 140, at least about 150, at least about 200, at least about 250, at least about 300, at least about 320, at least about 330, at least about 340, at least about 350, at least about 400, at least about 425, at least about 450, at least about 475, or at least about 500 base pairs in length is amplified to produce an amplified nucleic acid. In some examples, a region that is about 50-500 base pairs in length (for example, about 100-500 base pairs, about 100-150 base pairs, about 110-130 base pairs, about 200-350 base pairs, about 300-350 base pairs, about 320-340 base pairs, or about 120 base pairs, about 250 base pairs, about 325 base pairs, or about 475 base pairs in length) is amplified. In some specific examples the region of the influenza virus PB1 nucleic acid is amplified using at least one primer to produce an amplified PB1 nucleic acid of at least about 50, at least about 60, at least about 70, at least about 80 at least about 90, at least about 100, at least about 110, at least about 120, at least about 130, at least about 140, at least about 150, at least about 200, at least about 250, at least about 300, at least about 320, at least about 330, at least about 340, at least about 350, at least about 400, at least about 425, at least about 450, at least about 475, or at least about 500 base pairs in length (for example, about 50-500 base pairs, about 100-500 base pairs, about 100-150 base pairs, about 110-130 base pairs, about 200-350 base pairs, about 300-350 base pairs, about 320-340 base pairs, or about 120 base pairs, about 250 base pairs, about 325 base pairs, or about 475 base pairs in length).

Any nucleic acid amplification method can be used to detect the presence of influenza virus nucleic acids in a sample. In one specific, non-limiting example, polymerase chain reaction (PCR) is used to amplify an influenza virus PB1 nucleic acid or portion thereof. In other specific, non-limiting examples, real-time PCR, reverse transcriptase-polymerase chain reaction (RT-PCR), real-time reverse transcriptase-polymerase chain reaction (rt RT-PCR), ligase chain reaction, transcription-mediated amplification (TMA), cell cloning, or cell-based DNA cloning is used to amplify the nucleic acids. In a specific example, an influenza virus PB1 nucleic acid or portion thereof is amplified by reverse transcriptase-PCR. In another example, an influenza virus PB1 nucleic acid is amplified by real-time PCR, for example real-time TAQMAN® PCR. Techniques for nucleic acid amplification are well-known to those of ordinary skill in the art. Other examples of nucleic acid amplification techniques include quantitative real-time PCR; nested PCR; strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see Eur. Pat. Publ. EP320308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others. Additional amplification techniques include cell cloning and cell-based DNA cloning (see Strachan and Read, *Human Molecular Genetics*, 2nd edition, Wiley-Liss, 1999).

Typically, at least two primers are utilized in the amplification reaction. In some examples, amplification of the influenza virus nucleic acid involves contacting a sample including a nucleic acid with one or more primers (such as two or more primers) that are capable of hybridizing to and directing the amplification of an influenza virus nucleic acid, such as a primer capable of hybridizing to an influenza virus nucleic acid sequence set forth as any one of SEQ ID NOs: 1-3 or a portion thereof (or a sequence with at least 70% identity to one of SEQ ID NOs: 1-3 or a portion thereof), for example a primer that is least 70% identical (such as at least 75%, 80%, 85%, 90%, 91%, 92%, 93%, 94%, 95%, 96%, 97%, 98%, 99%, or 100% identical) to the nucleotide sequence set forth as one of SEQ ID NO: 4, SEQ ID NO: 5, SEQ ID NO: 9, or SEQ ID NO: 10.

In one example, an influenza virus PB1 nucleic acid is amplified utilizing a pair of primers, such as a forward primer at least 70% identical to SEQ ID NO: 4 and a reverse primer at least 70% identical to SEQ ID NO: 5, such as a forward primer consisting essentially of or consisting of SEQ ID NO: 4 and a reverse primer consisting essentially of or consisting of SEQ ID NO: 5. In another example, an influenza virus PB1 nucleic acid is amplified utilizing a pair of primers, such as a forward primer at least 70% identical to SEQ ID NO: 9 and a reverse primer at least 70% identical to SEQ ID NO: 10, such as a forward primer consisting essentially of or consisting of SEQ ID NO: 9 and a reverse primer consisting essentially of or consisting of SEQ ID NO: 10. In another example, an influenza virus PB1 nucleic acid is amplified utilizing a pair of primers, such as a forward primer at least 70% identical to SEQ ID NO: 9 and a reverse primer at least 70% identical to SEQ ID NO: 5, such as a forward primer consisting essentially of or consisting of SEQ ID NO: 9 and a reverse primer consisting essentially of or consisting of SEQ ID NO: 5.

Although exemplary primer sequences are provided in SEQ ID NOs: 4, 5, 9, and 10, the primer sequences can be varied slightly by moving the primer a few nucleotides upstream or downstream from the nucleotide positions that they hybridize to on the target nucleic acid molecule, provided that the primer is still capable of hybridizing and directing amplification of the target nucleic acid sequence, for example capable of hybridizing to at least one of SEQ ID NOs: 1-3. For example, variations of any of the primers disclosed as SEQ ID NOs: 4, 5, 9, and 10 can be made by "sliding" the primers a few nucleotides 5' or 3' from their positions, and such variation will still be specific for the respective target nucleic acid sequence. The primer sequence can also be varied by adding or removing one or more nucleotides (for example, 1, 2, 3, 4, or more) at the 5' and/or the 3' end, and such variations will still be specific for the target nucleic acid sequence.

Also provided by the present disclosure are primers that include variations to the nucleotide sequences shown in any of SEQ ID NOs: 4, 5, 9, and 10, as long as such variations permit hybridization to and amplification of the target nucleic acid molecule (for example, at least one of SEQ ID NOs: 1-3 or a portion thereof). For example, a primer can have at least 70% sequence identity such as at least 75%, 80%, 85%, 90%, 91%, 92%, 93%, 94%, 95%, 96%, 97%, 98%, or 99% identity to a nucleic acid consisting of the sequence shown in SEQ ID NOs: 4, 5, 9, or 10. In such examples, the number of nucleotides does not change, but the nucleic acid sequence shown in any or SEQ ID NOs: 4, 5. 9, and 10 can vary at a few nucleotides, such as changes at 1, 2, 3, or 4 nucleotides.

In some embodiments, the primers are degenerate at one or more positions (such as 1, 2, 3, 4, 5, or more positions), for example, a primer that includes a mixture of nucleotides (such as 2, 3, or 4 nucleotides) at a specified position in the primer. In some examples, the primers include at least one position with a degenerate position (designated "N") including a substantially equal mixture of each of A, C, G, and T nucleotides. In other examples, the ratio of the four nucleotides can be varied. In some examples, the primers include one or more synthetic bases or alternative bases (such as inosine (I)). In other examples, the primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). The disclosed primers may also include a combination of one or more degenerate bases, synthetic or alternative bases, and/or modified nucleotides.

Detecting the amplified product can be by any method known to one of ordinary skill in the art. In some examples, the amplified PB1 nucleic acid is detected by gel electrophoresis (such as slab gel electrophoresis or capillary gel electrophoresis). In some examples, one or more of the disclosed primers include a detectable label. In other examples, the amplified PB1 nucleic acid is detected by the use of one or more labeled probes that are sufficiently complementary to and specifically hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as an influenza virus PB1 nucleic acid, includes the combined use of PCR amplification and a labeled probe such that the product is measured using real-time PCR (such as TAQMAN® real-time PCR). In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In still further embodiments, the detection of amplified target nucleic acid sequence of interest includes the hybridization of a labeled amplified target nucleic acid to one or more probes that are arrayed in a predetermined array with an addressable location and that are complementary to the amplified target nucleic acid.

In some embodiments, the primer or probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with an amplified influenza virus reaction mixture or product, and hybridization is determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some embodiments, the disclosed methods include additional steps, for example for determining a particular type of subtype of influenza virus in a sample. In some examples, the amplified PB1 nucleic acid is sequenced and the sequence is compared to known influenza virus PB1 sequences (for example using BLAST or multiple sequence alignment tools). The type (such as influenza A, influenza B, influenza C, or a novel influenza virus) can be determined by similarity to known influenza virus sequences. In other examples, the sample can be analyzed by subsequent or simultaneous additional methods, such as amplification and/or detection of particular influenza type or subtype specific nucleic acids (such as PB1, HA, NA, or other nucleic acids). Some exemplary additional assays include commercially available influenza diagnostics, such as Rapid Detection Flu A+B (3M, St. Paul, Minn.), DIRECTIGEN™ Flu A+B (BD Diagnostics, Sparks, Md.), and SAS FluAlert tests (SA Scientific, San Antonio, Tex.). See also, Huang et al., *J. Clin. Microbiol.* 47:390-396, 2009; Percivalle et al., *New Microbiologica* 31:319-327, 2008. One of ordinary skill in the art can select appropriate additional assays.

IV. Primers

Primers capable of hybridizing to and directing the amplification of an influenza virus PB1 nucleic acid are disclosed herein. The primers are between 10 to 40 (for example, 20 to 35 or 15 to 30) nucleotides in length, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or even 40 nucleotides in length. In some examples, the primers are at least 10, 15, 20, 25, 30, 35, or 40 nucleotides in length. In other examples, the primers may be no more than 10, 15, 20, 25, 30, 35, or 40 nucleotides in length.

In several embodiments, a primer is capable of hybridizing under low, high, or very high stringency conditions to an influenza virus nucleic acid, such as an influenza virus PB1 nucleic acid, such as an influenza A virus PB1 nucleic acid, an influenza B virus PB1 nucleic acid, an influenza C virus PB1 nucleic acid, or two or three thereof and directing the amplification of the influenza virus nucleic acid molecule. In some examples, the primer is capable of hybridizing under high or very high stringency conditions to an influenza virus PB1 nucleic acid with a sequence set forth as any one of SEQ ID NOs: 1-3, and directing the amplification of any one of SEQ ID NO: 1-3, or a subsequence thereof. In other examples, a primer is capable of hybridizing under low stringency conditions to an influenza virus PB1 nucleic acid with at least 70% identity (such as at least 80%, 85%, 90%, 95%, or more identity) to a sequence set forth as any one of SEQ ID NOs: 1-3, and directing the amplification of the nucleic acid with at least 70% identity to SEQ ID NO: 1-3, or a subsequence thereof.

In several embodiments, a primer capable of hybridizing to and directing the amplification of an influenza virus PB1 nucleic acid molecule or a portion thereof includes a nucleic acid sequence that is at least 70% identical, such as at least 75%, 80%, 85%, 90%, 91%, 92%, 93%, 94%, 95%, 96%, 97%, 98%, 99%, or even 100% identical, to the nucleic acid sequence set forth as ACIGGAGACAAIACNAAATG-GAATGA (SEQ ID NO: 4) or ACTGTTGACAGCATITT-NAACATNCCC (SEQ ID NO: 5) or the complement thereof, wherein "I" is inosine and "N" is a degenerate position including A, C, G, and T. In several embodiments, a primer capable of hybridizing to and directing the amplification of an influenza virus PB1 nucleic acid molecule or a portion thereof consists essentially of, or consists of a nucleic acid sequence set forth as SEQ ID NO: 4 or SEQ ID NO: 5, or the complement thereof.

In other embodiments, a primer capable of hybridizing to and directing the amplification of an influenza virus PB1 nucleic acid molecule or a portion thereof includes a nucleic acid sequence that is at least 70% identical, such as at least 75%, 80%, 85%, 90%, 91%, 92%, 93%, 94%, 95%, 96%, 97%, 98%, 99%, or even 100% identical, to the nucleic acid sequence set forth as CCAGTTGGAGGIAATGA-RAAGAANGC (SEQ ID NO: 9) or CATTCATTCCATT-TIGTRTTRTCNCC (SEQ ID NO: 10) or the complement thereof, wherein "I" is inosine; "N" is a degenerate position including A, C, G, and T; and "R" is a purine (e.g., adenine or guanine). In several embodiments, a primer capable of hybridizing to and directing the amplification of an influenza virus PB1 nucleic acid molecule or a portion thereof consists essentially of, or consists of a nucleic acid sequence set forth as SEQ ID NO: 9 or SEQ ID NO: 10, or the complement thereof.

V. Kits

The nucleic acid primers and/or probes disclosed herein can be supplied in the form of a kit for use in the detection of an influenza virus or related virus in a sample. In one example, an appropriate amount of one or more of the nucleic acid primers disclosed herein (for example a primer at least 70% identical to SEQ ID NO: 4, SEQ ID NO: 5, SEQ ID NO: 9, or SEQ ID NO: 10) is provided in one or more containers. A nucleic acid primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. One or more control probes, primers, and/or templates for use in the PCR reactions also may be supplied in the kit.

In some examples, a kit includes one or more sets of primers (such as the primers described above), such as a pair of primers, for example in pre-measured single use amounts in individual, typically disposable, tubes or equivalent containers. With such an arrangement, the sample to be tested for the presence of the target nucleic acids can be added to the individual tube(s) and amplification carried out directly. In some examples, the kit includes a pair of primers with a sequence at least 70% identical to SEQ ID NOs: 4 and 5. In some examples, the kit includes a pair of primers consisting of the sequence set forth as SEQ ID NO: 4 and SEQ ID NO: 5. In additional examples, the kit includes a pair of primers with a sequence at least 70% identical to SEQ ID NOs: 9 and 10. In some examples, the kit includes a pair of primers consisting of the sequence set forth as SEQ ID NO: 9 and SEQ ID NO: 10. In still further examples, the kit includes two or more pairs of primers, such as SEQ ID NOs: 4, 5, 9, and 10.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of target nucleic acid molecules, such as additional pathogen and/or human nucleic acids.

In some embodiments, kits also may include the reagents necessary to carry out PCR amplification reactions, including nucleic acid sample preparation reagents, appropriate buffers (such as polymerase buffer), salts (for example, magnesium chloride), deoxyribonucleotides (dNTPs), reverse transcriptase, and/or polymerases.

In particular embodiments, the kit includes prepackaged primers, such as primers suspended in suitable medium in individual containers (for example, individually sealed tubes). In some examples, the primers include those provided herein. In other particular embodiments, the kit includes equipment, reagents, and instructions for extracting and/or purifying nucleotides from a sample.

The present disclosure is illustrated by the following non-limiting Examples.

EXAMPLE 1

Detection of Novel Influenza Virus in Guatemalan Bats

Methods

Guatemala was chosen as one major comparative New World study location in Central America as part of the CDC Global Disease Detection program. Animal capture was designed to provide preliminary background information on etiological associations and disease ecology at the interface of humans, domestic animals, and wildlife. Project protocols for animal capture and use were approved by the CDC Animal Care and Use Committee and the Ethics and Animal Care and Use Committee of the Universidad del Valle de Guatemala (Guatemala City, Guatemala). Locales for sampling bats were chosen on the basis of historical outbreaks of bovine paralytic rabies based upon national surveillance data, or by proximity to villages with known or suspected vampire bat predation upon human populations. Bats were captured manually by using mist and hand nets. Representative samples at each site consisted of adults and juveniles of both sexes. After euthanasia, a complete necropsy was performed on all bats in compliance with approved field protocols. Samples included blood, major organs (liver, intestine, lung and kidney), rectal and oral swabs. Samples were stored immediately on dry ice in the field and later were maintained at −80° C. in the laboratory until processing. Total nucleic acids (TNA) were extracted from 200 µl of phosphate buffered saline suspension of each swab by using the QIAAMP® MINELUTE® Virus Spin kit (Qiagen, Valencia, Calif.), and then stored at −80° C.

TNA extracted from the rectal swabs (n=316) were screened for the presence of influenza virus RNA using pan-influenza (pan-Flu) reverse transcriptase PCR (RT-PCR) with consensus degenerate primers targeting a conserved region of PB1 in the influenza virus genome (Table 1). Conserved amino acid sequences of influenza virus PB1 were selected from alignment of deduced protein coding sequences available in GenBank. A total of 162 influenza virus PB1 sequences (110 influenza A, 28 influenza B, and 24 influenza C sequences) were aligned using ClustalW. Highly conserved domains between 8 and 10 amino acids in length were back-translated into degenerate nucleotide sequences to represent all possible codons for the corresponding amino acids. Primers were designed with mixed degenerate bases restricted to between 9 and 12 nucleotides in the 3' portion of the primer and inosine (maximum of four) and consensus nucleotides for the middle and 5' portion of the primer. To minimize the potential for non-specific cross-reactivity, a Blastn search analysis was performed to identify primers with similarity to known sequences.

The optimized RT-PCR mixtures contained 2 µM each of forward and reverse primers, 1× buffer with a final concentration of 2.0 mM MgSO$_4$ and 0.2 mM (each) deoxynucleoside triphosphates, 20 U of RNase inhibitor, a 5 µl aliquot of TNA extracts, and 2 µl of SUPERSCRIPT™ III RT/Platinum Taq mix from the SUPERSCRIPT™ III One-Step RT-PCR kit (Invitrogen, Carlsbad, Calif.). The amplification procedure consisted of 30 minutes at 50° C., followed by 2 minutes at 94° C., 40 cycles for 15 seconds at 94° C., 30 seconds at 50° C. and 1 minute at 72° C., and a final extension at 72° C. for 7 minutes in an automated thermal cycler. Positive and negative RT-PCR controls containing standardized viral RNA extracts and nuclease-free water were included in each run. Standard precautions were taken to avoid cross-contamination of samples before and after RNA extraction and amplification. Each of the positive results was repeated and confirmed from different TNA aliquots of the original bat rectal swab eluate. The resulting PCR amplicons were separated by electrophoresis in agarose gel and purified using QIAQUICK® PCR Purification kit or QIAQUICK® Gel Extraction kit (Qiagen). Purified DNA amplicons (both strands) were then sequenced with the RT-PCR primers on an ABI Prism 3130 automated capillary sequencer (Applied Biosystems, Foster City, Calif.).

TABLE 1

Pan-influenza RT-PCR primers

| Primer | Sequence (5' -> 3') | SEQ ID NO: |
|---|---|---|
| Flu-Pan-F3 | ACIGGAGACAAIACNAAATGGAATGA | 4 |
| Flu-Pan-R4-2 | ACTGTTGACAGCATITTNAACATNCCC | 5 |

I = inosine;
N = degenerate base (mixture of A, C, G, and T)

The primers and TAQMAN® probe for a quantitative-RT-PCR (qRT-PCR) assay were designed for targeting the nucleoprotein (NP) of the novel bat virus. The specificity of primers and probe was tested using a BLAST search against the Genbank database to assess potential cross hybridization with other influenza virus species and other non-target organisms. The qRT-PCR assays were performed on the MX3005P (Agilent Technologies) using the SUPERSCRIPT III™ Platinum One-step Quantitative RT-PCR system, The optimized qRT-PCR mixtures were run in a total reaction volume of 25 µl which contained 0.2 µM each of forward and reverse primers, 0.1 µM probe, 1× buffer with a final concentration of 6.0 mM MgSO$_4$ and 0.2 mM (each) deoxynucleoside triphosphates, 5 U of RNase inhibitor, a 5 µl aliquot of TNA extracts, and 2 µl of SUPERSCRIPT III™ RT/Platinum Taq mix. The two primers and the probe are GTM Flu NP For (CCATTATGAGGGTCCCCACT; SEQ ID NO: 6), GTM Flu NP Rev (GGATGTGCTCGTTGAT-GCA; SEQ ID NO: 7) and GTM Flu NP probe(FAM) (TCCCAGCTGCTCCAGCTCTTCTT; SEQ ID NO: 8), respectively. The amplification procedure consisted of 30 minutes at 45° C., followed by 5 minutes at 94° C., 40 cycles for 15 seconds at 94° C., and 60 seconds at 60° C. Standards were prepared from ten-fold serial dilutions of the NP constructs with known concentration. Negative controls without template were run on each plate using nuclease-free water. All standards, samples and controls were carried out in triplicate. The standard template was constructed from the cloned NP segment where the primers and probe are located. Unknown sample concentrations were calculated from a standard curve of templates of known concentration analyzed on the same plate. A sample was considered positive when more than one of three reactions was positive.

Results

A total of 316 bats from 21 different species were captured from eight locations in southern Guatemala in two consecutive years (180 bats in May, 2009, and 136 bats in September, 2010). Three of 316 bat rectal swabs were positive by the pan-influenza RT-PCR assay. All three were collected from little yellow-shouldered bats (*Sturnira lilium*, family Phyllostomidae), a frugivorous bat that is abundant throughout Central and South America. Two of the positive samples were from two of 15 little yellow-shouldered bats (bats GU09-153 and GU09-164) captured during 2009 at El Jobo, Guatemala, and the third was from one of 14 little yellow-shouldered bats (bat GU10-060) captured during 2010 from Agüero, Guatemala, located ~50 km from El Jobo. Each of the three samples was estimated by quantitative real-time RT-PCR (qRT-PCR) to have about $10^5$-$10^6$ viral genome copies per 100 µL of rectal swab suspension. Of the other available specimens (liver, intestine, lung, and kidney tissues and an oral swab from bat GU09-164), the four tissue specimens were positive, but the oral swab specimen was negative. These data support an infectious process rather than transit of ingested infected material through the digestive tract as the source of viral RNA, particularly because this bat species does not feed on other vertebrates. The nucleotide sequences of the 250-bp diagnostic PB1 amplicons from three different bat rectal samples were very similar to each other and by BLASTn search were most closely related to influenza A virus PB1 genes.

Figure 1B:
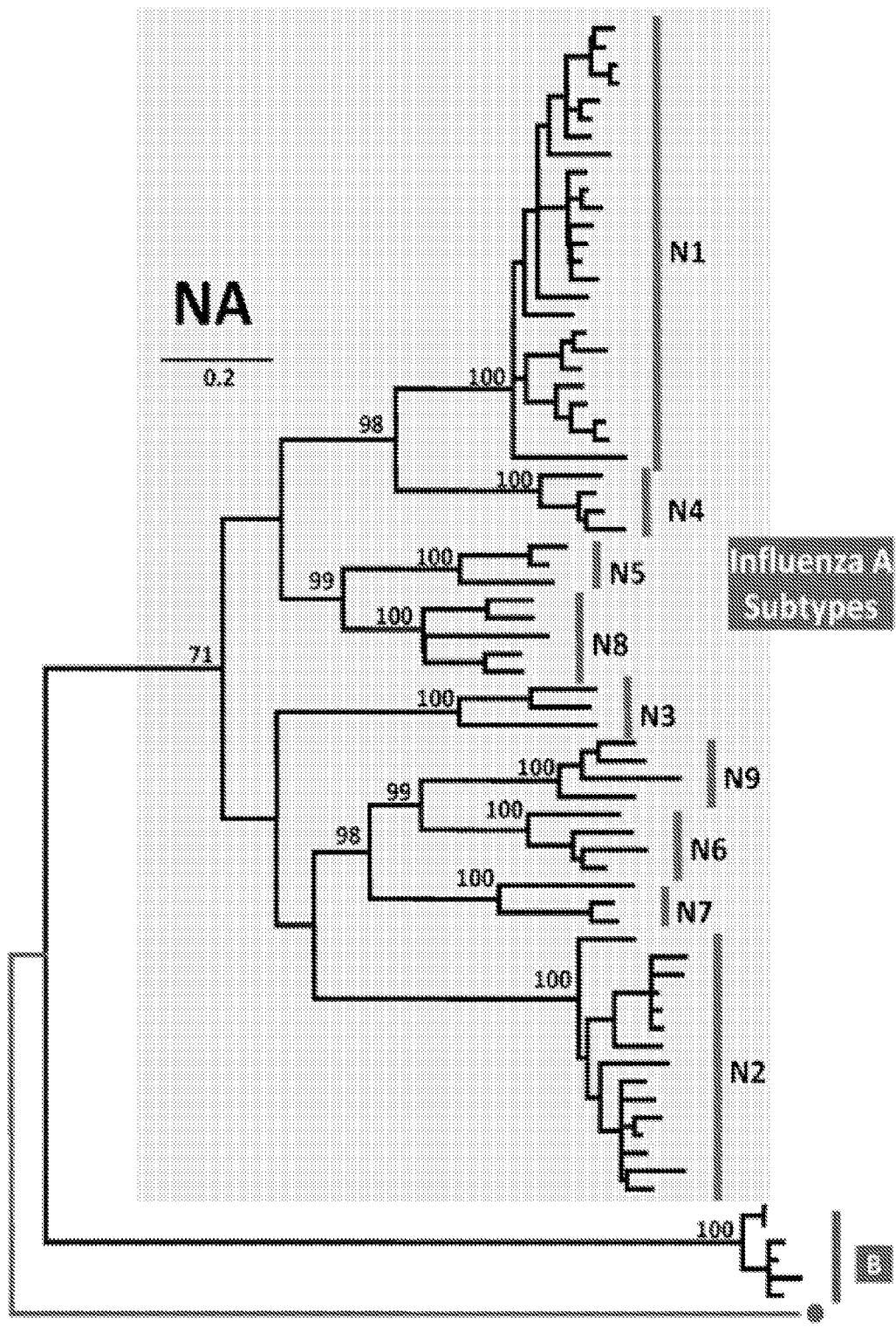
Figure 1C:
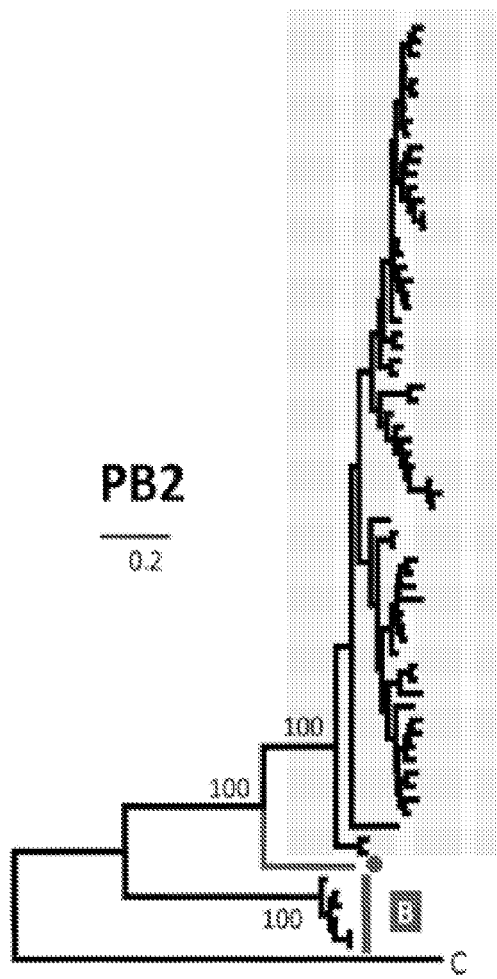
Figure 1D:
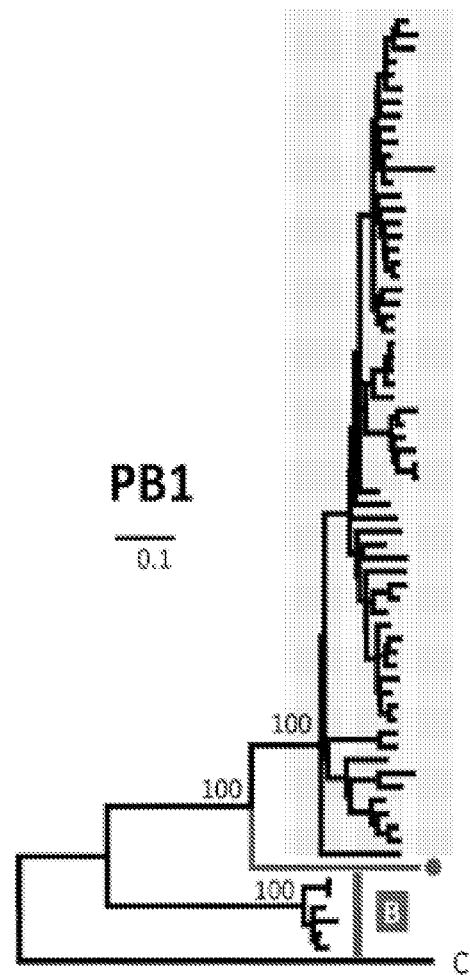
Figure 1E:
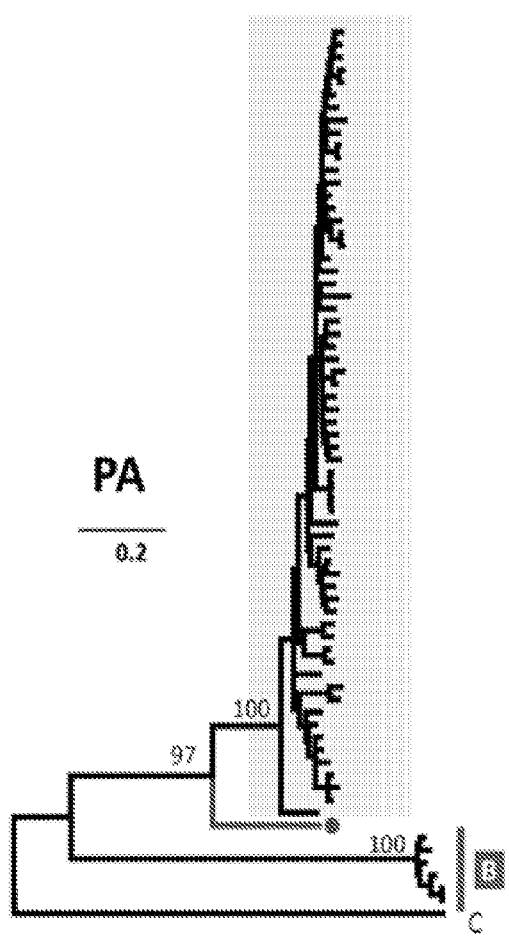
Figure 1F:
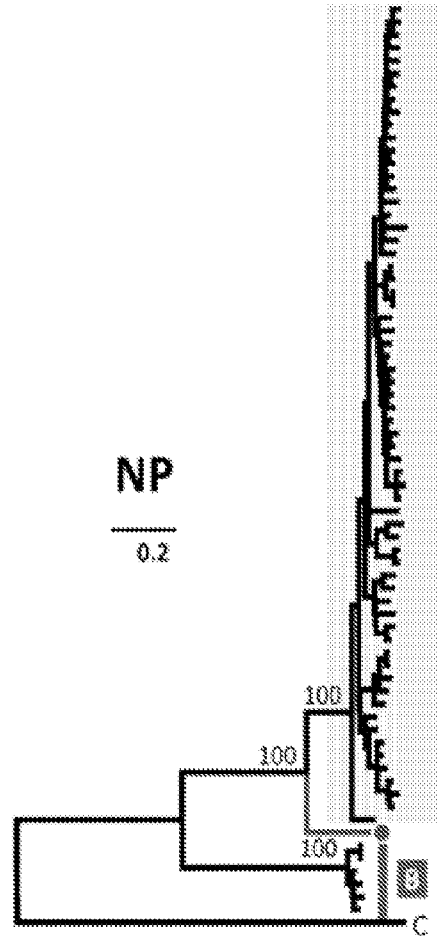
Figure 1G:
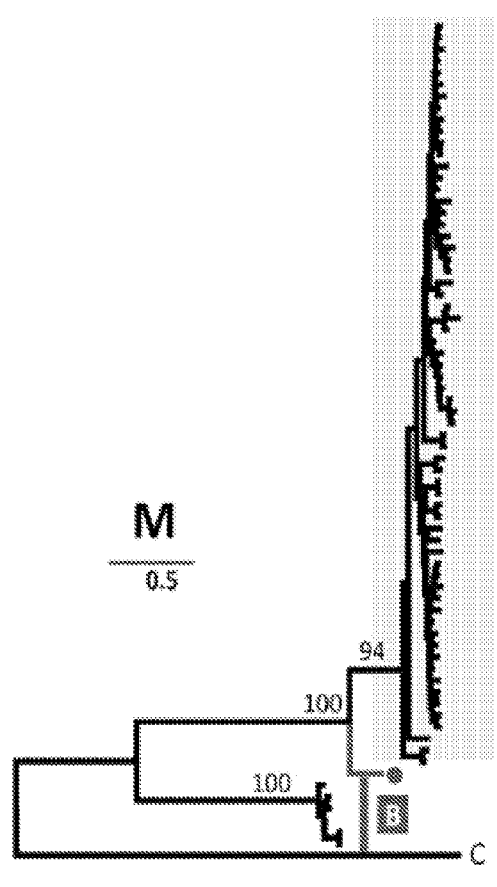
Figure 1H:
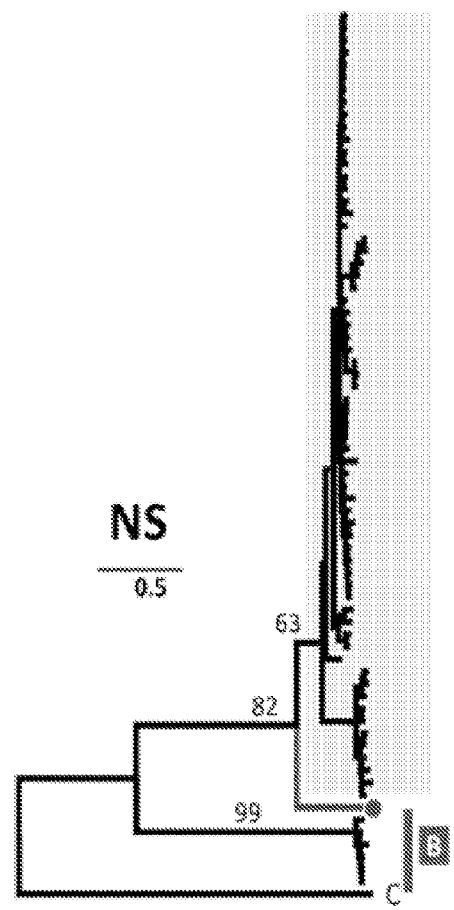

The full genome of the identified bat influenza viruses were sequenced (Tong et al., Proc. Natl. Acad. Sci. USA 109:4269-4274, 2012, incorporated herein by reference). The alignment and phylogenetic analysis of the bat viruses included a representative sample comprising 66 known influenza A viruses, six influenza B viruses, and one influenza C virus. Phylogenetic analyses of the eight gene segments using maximum-likelihood methods (FIG. 1A-H) and Bayesian inferences showed three distinctive types of relationships between genes of A/bat/Guat/09 and the known influenza viruses. Analysis of influenza A and B HA genes suggested that the A/bat/Guat/09 HA is more closely related to the Group 1 HAs (subtypes H1, 2, 5, 6, 8, 9, 11, 12, 13, and 16) than to the Group 2 HAs (H3, 4, 7, 10, 14, and 15) (FIG. 1A), sharing ancestry with a monophyletic clade containing H1, H2, H5, and H6 subtypes. Analysis of the A/bat/Guat/09 NA indicated that it was highly divergent from both influenza A and B NA genes sharing an older ancestral relationship to known influenza viruses (FIG. 1B). In contrast, the six so-called "internal" genes (PB2, PB1, PA, NP, M, and NS) of A/bat/Guat/09 were clustered outside the influenza A and B gene branches. Their positions in the phylogenetic tree were between the influenza A and B split but were related more closely to the type A viral genes (FIG. 1C-H).

EXAMPLE 2

Pan-Flu RT-PCR Detects Influenza A, B, and C

Methods

The reference viruses or viral RNA used in this study are listed in Table 2 and include 25 reference viruses from influenza virus A, 6 reference viruses from influenza virus B and 3 reference viruses from influenza virus C. RNAs were extracted from 100 µl of supernatant fluid of virus-infected cells with the QIAAMP® viral RNA kit (Qiagen, Santa Clarita, Calif.) according to the manufacturer's instructions. The RNA was eluted from the column in 50 µl of RNase-free water.

TABLE 2

Reference influenza viruses

| Ref. No. | Reference Virus Strain | Taxonomy Group | Subtype |
|---|---|---|---|
| 1 | A/New Caledonia/20/99 | FluA | H1N1 |
| 2 | A/Johannesburg/82/96 | FluA | H1N1 |
| 3 | A/Panama/2007/99 | FluA | H3N2 |
| 4 | A/Sydney/5/97 | FluA | H3N2 |
| 5 | A/Tky/Kansas/4880/80 | FluA | H1N1 |
| 6 | A/Dk/Nan/2-0485/2000 | FluA | H2N9 |
| 7 | A/Environ/NY/19019-6/98 | FluA | H3N8 |
| 8 | A/Tky/Eng/69 | FluA | H3N2 |
| 9 | A/Dk/NJ/5406-27/94 | FluA | H4N8 |
| 10 | A/Ql/NY/13989-51/98 | FluA | H7N2 |
| 11 | A/Tky/VA/4529/2002 | FluA | H7N? |
| 12 | A/Ck/PA/13552-1/98 | FluA | H7N2 |
| 13 | A/Tky/Ontario/6118/67 | FluA | H8N4 |
| 14 | A/Ck/Germany"N"/49 | FluA | H10N7 |
| 15 | A/Ck/NJ/1996 | FluA | H11N1 |
| 16 | A/Dk/Alberta/60/76 | FluA | H12N5 |
| 17 | A/Whale/ME/328/84 | FluA | H13N2 |
| 18 | A/Duck/Gurjev/263/82 | FluA | H14N5 |
| 19 | A/Shearwater/W Australia/2576/79 | FluA | H15N6 |
| 20 | A/HK/156/97 | FluA | H5N1 |
| 21 | A/Dk/Anyang/2001 | FluA | H5N1 |
| 22 | A/Teal/HK/W312/97 | FluA | H6N1 |
| 23 | A/PekinRobin/CA/30412/94 | FluA | H7N1 |
| 24 | A/HK/1073/99 | FluA | H9N2 |
| 25 | A/Ck/HK/G9/97 | FluA | H9N2 |
| 1 | B/HK/330/01(VA) | Flu B | |
| 2 | B/HK/330/01(NM) | Flu B | |
| 3 | B/Shizouka/15/01 | Flu B | |
| 4 | B/Sichuan/379/99 | Flu B | |
| 5 | B/Victoria/87 | Flu B | |
| 6 | B/Yamagata/16/88 | Flu B | |
| 1 | C/Taylor/1233/47 | Flu C | |
| 2 | C/Yamagata/11/81 | Flu C | |
| 3 | C/Yamagata/64 | Flu C | |

RT-PCR was performed using the pan-influenza primers described in Example 1 (Table 1, above). The RT-PCR mixtures contained 2 µM each of forward and reverse primers, 1× buffer with a final concentration of 2.0 mM $MgSO_4$ and 0.2 mM (each) deoxyribonucleotide triphosphates, 20 U of RNase inhibitor, a 5 µl aliquot of RNA extracts, and 2 µl of SUPERSCRIPT™ III RT/Platinum Taq mix from the SUPERSCRIPT™ III One-Step RT-PCR kit (Invitrogen). The amplification procedure consisted of 30 minutes at 50° C., followed by 2 minutes at 94° C., 40 cycles for 15 seconds at 94° C., 30 seconds at 50° C. and 1 minute at 72° C., and a final extension at 72° C. for 7 minutes in an automated thermal cycler. Positive and negative RT-PCR controls containing standardized viral RNA extracts and nuclease-free water were included in each run. Standard precautions were taken to avoid cross-contamination of samples before and after RNA extraction and amplification. The resulting PCR amplicons were separated by electrophoresis in agarose gel and purified using QIAQUICK® PCR Purification kit or QIAQUICK® Gel Extraction kit (Qiagen). Purified DNA amplicons (both strands) were then sequenced with the RT-PCR primers on an ABI Prism 3130 automated capillary sequencer (Applied Biosystems, Foster City, Calif.).

The sensitivity of the PCR assay was determined using a 10-fold dilution series of virus-infected cell culture (A/Tky/Kansas/4880/80) with known infectivity titers (PFU) and known copy numbers.

Results

Figure 2:
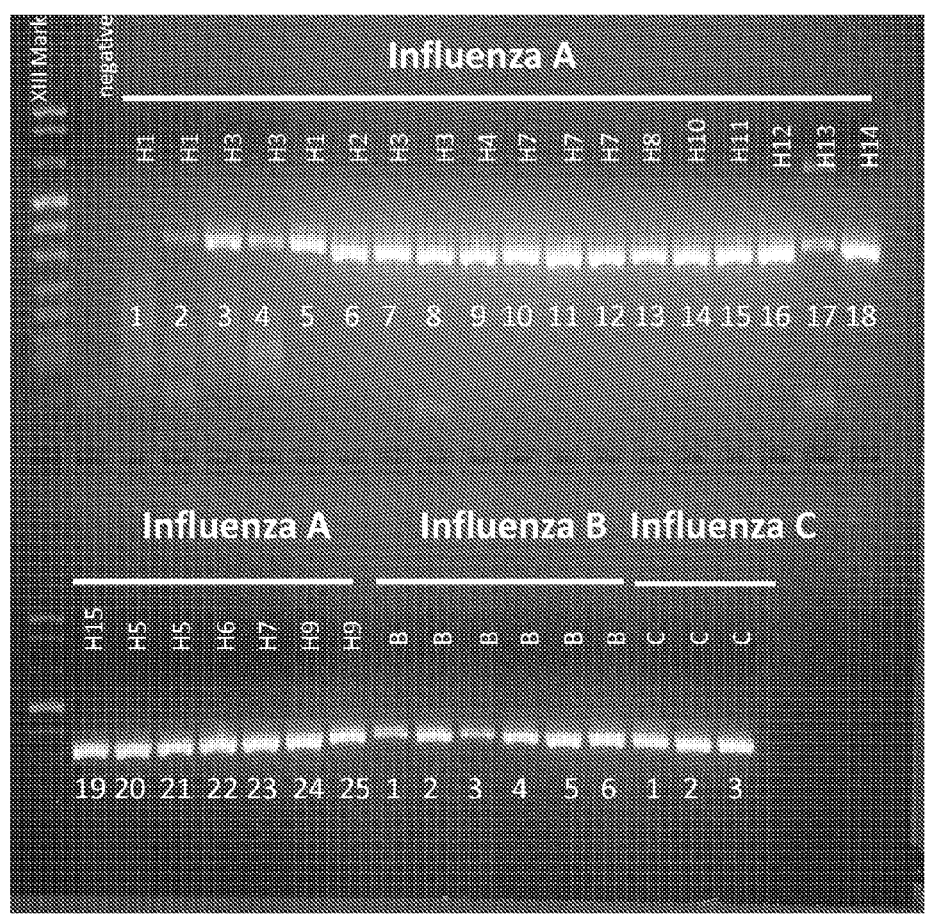
FIG. 2 is a digital image showing amplification of RNAs from 34 different viruses belonging to the genera Influenza virus A, Influenza virus B, and Influenza virus C by one step RT-PCR with the pan-influenza primer pair SEQ ID NOs: 4 and 5. The reference number of each virus (as designated in Table 2) is shown below each sample and the subtype is shown above each sample.

All of the 34 tested influenza reference viruses (representing 25 influenza A (H1-H15), 6 influenza B (both Yamagata and Victoria lineages) and 3 influenza C viruses) were successfully detected by RT-PCR with the pan-influenza primers (FIG. 2). The observed variation in amplicon intensity was probably due at least in part to differences in amount of template RNA for the respective viruses. No amplicon was detected for the PCR assays against the negative controls.

Figure 3:
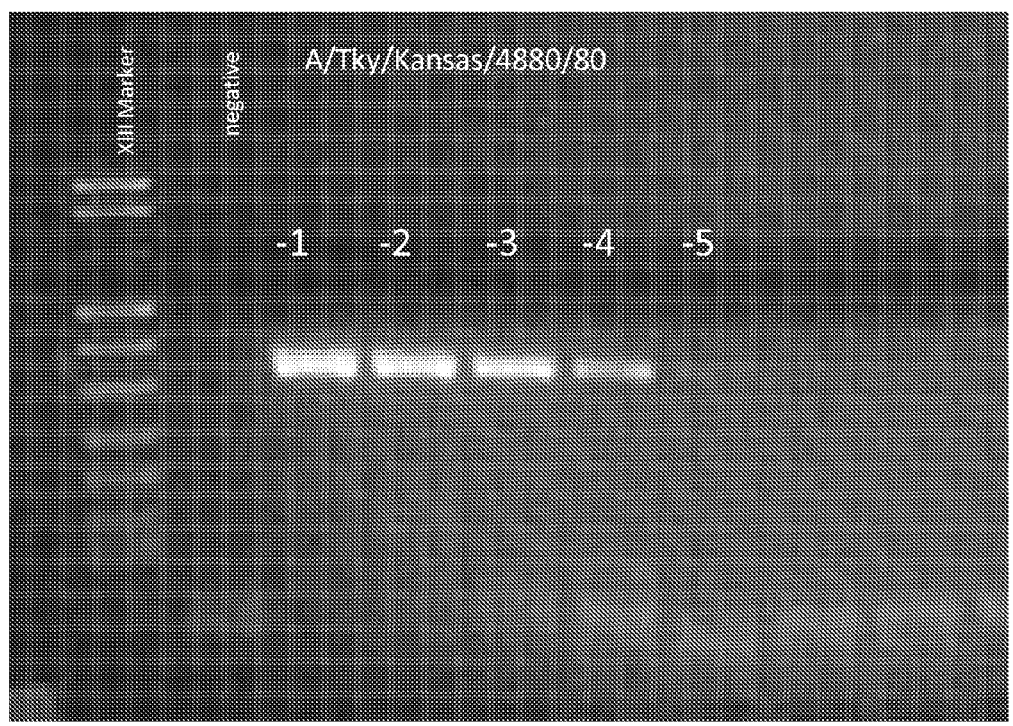
FIG. 3 is a digital image showing amplification of RNA extracted from 10-fold serial dilutions of A/Tky/Kansas/4880/80-infected cell culture with the pan-influenza primer pair SEQ ID NOs: 4 and 5. The fold-dilution ($10^{-1}$, $10^{-2}$, etc.) is shown above each sample.

To test the sensitivity of the RT-PCR assay, 10-fold serial dilutions of A/Tky/Kansas/4880/80 RNA with known copy numbers were tested (FIG. 3). The sensitivity limit was calculated as approximately 100-500 RNA copies.

EXAMPLE 3

Detection of Novel Influenza Viruses in Peruvian Bats

Materials and Methods

Sample Collection: Bats were restrained, sedated, and euthanized in accordance with established protocols as approved by the CDC Institutional and Animal Care and Use Committee and under a Peru Ministry of Agriculture permit RD-0389-2010-DGFFS-DGEFFS. CDC field sampling of selected mammals, such as bats, has been ongoing for several years as a means of background zoonotic surveillance for primary pathogen detection (Kuzman et al., *Vector Borne Zoonotic Dis.* 11:1465-1470, 2011). Field work was related to a reported high incidence of vampire bat predation in human communities in the Peruvian Amazon (Bai et al., *Am. J. Trop. Med. Hyg.* 87:518-523, 2012). Bat sampling was conducted for enhanced rabies surveillance related to concurrent human surveys, and to improve an understanding of pathogen diversity in the Neotropical bat fauna. Bats were captured manually and by using mist nets and hand nets; adults and subadults of both sexes were captured. After euthanasia, a complete necropsy was performed on all bats in compliance with established field protocols. A total of 114 bats from at least 18 different species were captured from Truenococha and Santa Marta, two communities in the Loreto Department of Peru at the edge of the Amazon River basin. Representative tissues were removed from bats. Samples of serum, tissues, organs, and rectal and oral swabs were immediately stored in liquid nitrogen in the field and then at −80° C. in the laboratory until processing and analysis. Total nucleic acids (TNA) were extracted from 200 µL of a phosphate buffered saline suspension of each swab by using the QIAAMP® MINELUTE® Virus Spin kit (Qiagen, Santa Clarita, Calif.), according to the manufacturer's instructions and then stored at −80° C.

Pan-Influenza RT-PCR: TNA extracted from the rectal swabs (n=110) were screened for the presence of influenza virus RNA using pan-influenza (pan-Flu) RT-PCR as described in Example 1. Positive and negative RT-PCR controls containing standardized viral RNA extracts and nuclease-free water were included in each run. Standard precautions were taken to avoid cross-contamination of samples before and after RNA extraction and amplification. Each of the positive results was repeated and confirmed from different TNA aliquots of the original bat rectal swab eluate. The resulting PCR amplicons were separated by electrophoresis in agarose gel and purified using QIAQUICK® PCR Purification kit or QIAQUICK® Gel Extraction kit (Qiagen). Purified DNA amplicons (both strands) were then sequenced with the RT-PCR primers on an ABI Prism 3130 automated capillary sequencer (Applied Biosystems).

Complete Genome Sequencing: The pan-Flu RT-PCR positive rectal swab suspension was subjected to both high throughput next generation sequencing and RT-PCR amplicon-based Sanger sequencing as described previously (Tong et al., *Proc. Natl. Acad. Sci. USA* 109:4269-4274, 2012, incorporated herein by reference). In brief, 200 µl of rectal swab suspension (in PBS) from the bat PEBT033 was first cleared through an ULTRAFREE® MC 0.22-µm filter (Millipore, Billerica, Mass.) and then extracted using the QIAAMP® MINELUTE® Virus Spin kit. The extracted TNA was randomly amplified using the Round AB protocol as previously described (Tong et al., *Proc. Natl. Acad. Sci. USA* 109:4269-4274, 2012). Amplification products were subjected to high-throughput sequencing by an Illumina GAIIx sequencer (Illumina, San Diego, Calif.). The resulting sequence was extracted and de-multiplexed using Illumina SCS2.8 software. The data were then analyzed using the CLC Genomics Workbench package. The imported reads were trimmed to remove low quality sequence as well as any reads of <36 bases in length. The reads were assembled de novo with a minimum contig length of 75 bases. All contigs with a coverage depth ≥3X where submitted to BLASTn against the non-redundant (nr) NCBI database to identify influenza sequences. This process was repeated with tBLASTx to find segments that were not identified from nucleotide BLASTn.

To increase the reliability of the sequence data from Illumina sequencing, the rectal swab of bat PEBT033 was also processed by Sanger sequencing on RT-PCR amplicons of genome segments. The viral genome was amplified directly from the TNA extracted from bat PEBT033 rectal swab suspensions using universal influenza A primers (FWuni12 and RVuni13; Inoue et al., *Microbiol. Immunol.* 54:129-134, 2010). The 800 by to 2.3 kb amplicons were then cloned using the pCR-XL-TOPO TA cloning kit (Invitrogen, Carlsbad, Calif.). Eight to 16 colonies from each of the 8 segments' RT-PCR transformation were first sequenced with M13 forward and reverse primers in both directions, and the remaining internal gaps were sequenced with sequence-specific walking primers in both directions. The 3' end and 5' end sequences of each segment from bat PEBT033 were determined using the 5'/3' RACE kit (Roche Applied Science, Mannheim, Germany) according to the manufacturer's instructions. Sequence analysis and generation of contigs were performed using Sequencher software (Gene Codes Software, Ann Arbor, Mich.). Consensus gene sequences were compared to those from the high throughput next generation sequencing methods. Sequence identification was performed through NCBI BLASTn and tBLASTx similarity searches.

Sequence Data Set: 8486 complete genome sequences of influenza A virus, comprising both avian and other mammalian hosts, were downloaded from the GISAID data base (available on the World Wide Web at platform.gisaid.org/epi3/frontend). Sequence alignment was performed on the amino acid sequences of each gene segment using MAFFT v6.853b (Katoh et al., *Nucl. Acids Res.* 30:3059-3066, 2002; Poole et al., *Virology* 321:120-133, 2004). Because of the highly divergent nature of the HA and NAL segments, all ambiguously aligned sites in these segments were removed using the G-blocks program (Talavera et al., *Syst. Biol.* 56:564-577, 2007). This resulted in the final alignment lengths for the HA and NAL proteins of 507 and 395 amino acids, respectively. Because of the very large number of sequences available from some subtypes, each amino acid alignment was further subsampled based on sequence similarity to obtain smaller data sets with between 300 and 400 representative sequences. Pairwise genetic distances were then estimated between these sequences using the JTT model of amino acid substitution available in the MEGA5 v5.05 package (Tamura et al., *Mol. Biol. Evol.* 56:564-577, 2011).

Phylogenetic Analysis: To assist phylogenetic analyses of these sequence data, the sample size was reduced to 50-70 representative sequences for each segment. Phylogenetic trees of these data were then estimated using the maximum likelihood (ML) method available in the PhyML package (Guindon et al., *Syst. Biol.* 59:307-321, 2010), employing 100 bootstrap replicates. In all cases, the JTT model of amino acid substitution was employed with four categories of gamma-distributed rate heterogeneity and a proportion of invariant sites (JTT+F4+I).

Figure 4A:
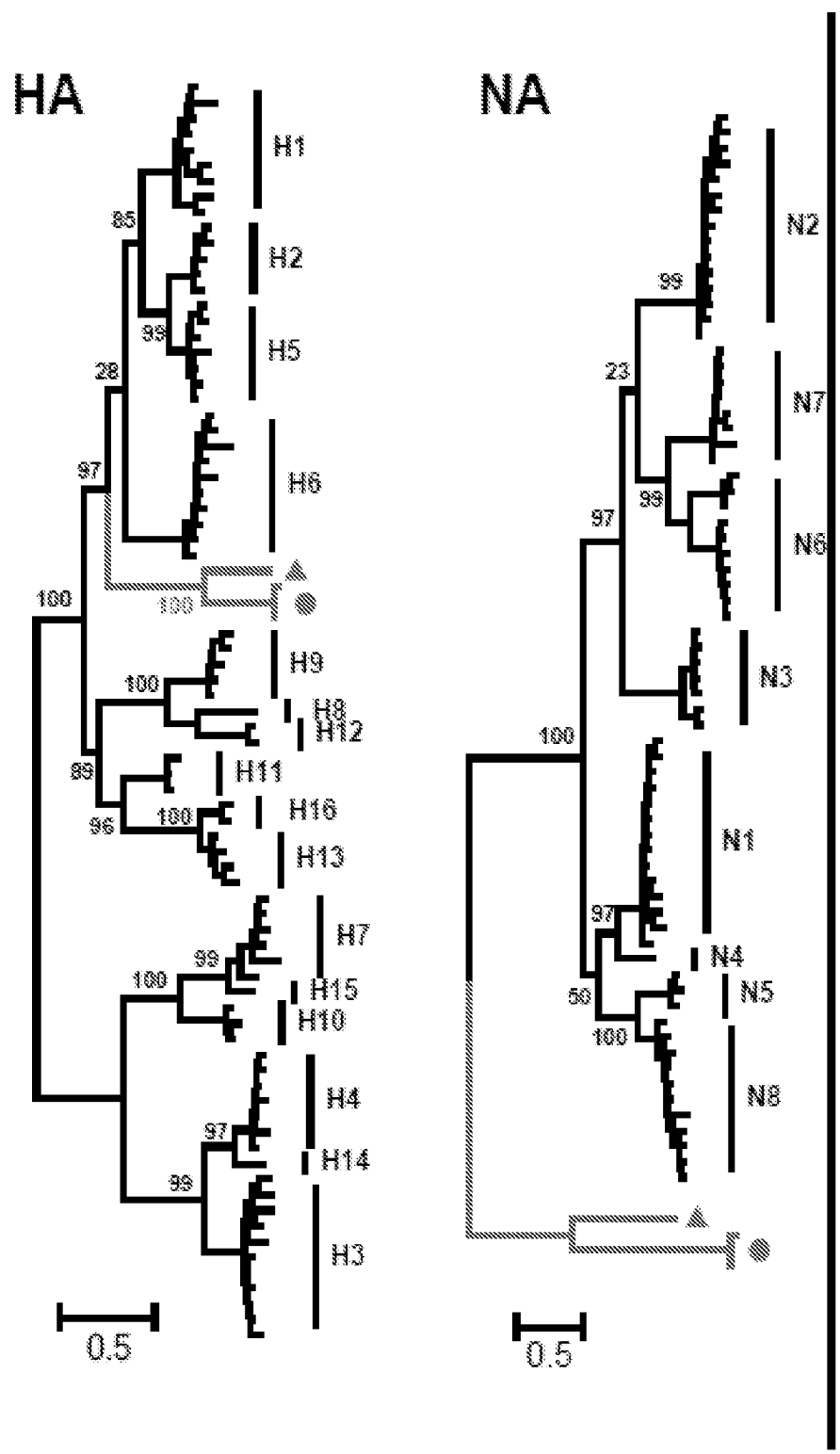
FIGS. 4A and B are a series of phylogenetic trees of the eight influenza A gene segments sampled from bats and other animals, based on the amino acid sequences of each gene segment. Trees are shown for HA and NA (FIG. 4A) and PB2, PA, MP, PB1, NP, and NS (FIG. 4B) gene segments. Triangle indicates the Peru bat isolate; circle indicates Guatemala bat isolates.
Figure 4B:
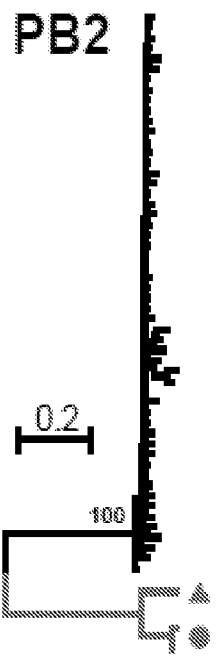
Figure 4B:
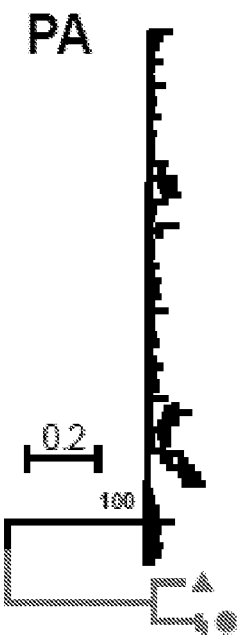
Figure 4B:
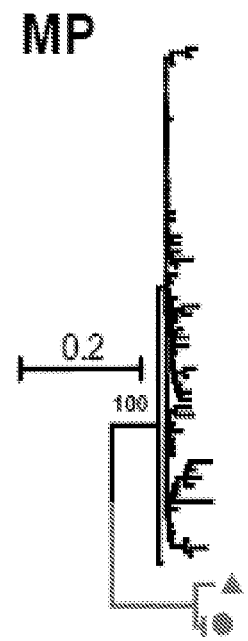
Figure 4B:
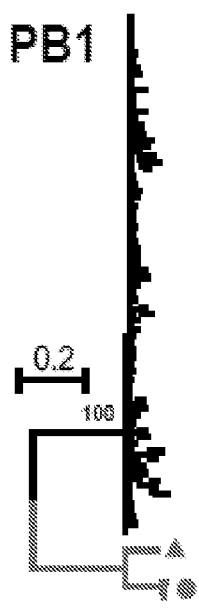
Figure 4B:
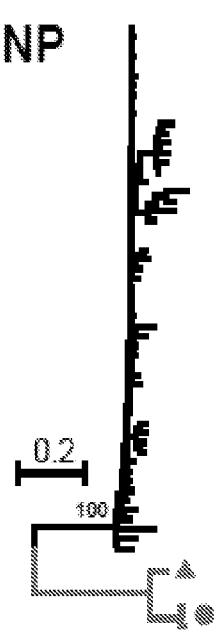
Figure 4B:
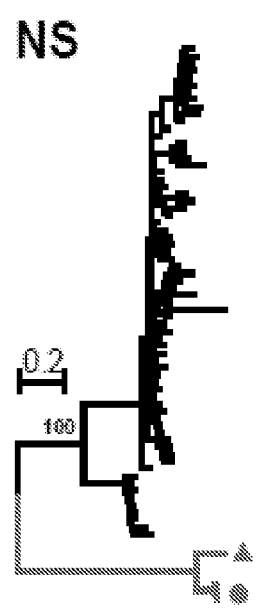

Analysis of Selection Pressure: To compare the selection pressures of influenza viruses in bats with those sampled in other hosts, we estimated the relative numbers of non-synonymous to synonymous substitutions per site (dN/dS) for each group of viruses in each segment. This analysis was performed using the branch-specific model available in the CODEML program implemented in PAML v4.4 (Yang, *Mol. Biol. Evol.* 35:1586-1591, 2007). Accordingly, it was specified, a priori, that branches sampled from within the bats are categorized as 'foreground' branch(es), with the remainder categorized as 'background' branches. dN/dS was then estimated separately for the foreground and background branches, with the significance of the difference between these estimates obtained using a likelihood ratio test (LRT).

ELISA: An indirect ELISA using bat influenza neuraminidase and hemagglutinin was run to establish the seroprevalence of IgG antibodies to bat influenza within the Peru bat population. In brief, ELISA plates were coated with recombinant bat hemagglutinin (rHA) or recombinant bat neuraminidase-like (rNAL) at a concentration of 1 μg/mL (100 μL per well) in PBS, pH 7.4 overnight at 4° C. The next morning, bat sera were heat inactivated at 56° C. for 30 minutes. Plates were washed 3 times with PBS with Tween 20 (0.1%), pH 7.4 (PBST). Bat sera were diluted 1:500 in 2.5% non-fat milk-PBST and added to each well in duplicate, two-fold dilutions. Plates were incubated for 1 hour at 37° C. The test sera were removed and the plates washed 3 times with PBST. Biotinylated protein G (MBL, Woburn, Mass.) (a 1:1,000 dilution of 1 mg/mL solution, 100 μL) was added to each well and the plates were incubated at 37° C. for 1 hour. The plates were washed 3 times with PBST. Streptavidin HRP (Millipore, Billerica, Mass.) (a 1:10,000 dilution of 1 mg/mL solution, 100 μL) was added to each well and the plates were incubated at 37° C. for 1 hour. The plates were washed 3 times with PBST and 0-phenylenediamine with H2O2 added to each well (100 μL). The plates were incubated at 37° C. for 10 minutes, the color change was stopped by addition of 3N HCl, and the plates read by a plate reader (490 nm, 0.1 s). The limit of detectable response (based on 490 nm at 0.1 s OD) for the ELISA was set as values above average background plus 2 standard deviations.

Results

114 Peruvian bats captured during 2010 in Truenococha and Santa Marta, two communities located in the Loreto Department, Peru, a remote and sparsely populated area in Amazonia were sampled. The sampled bats comprised 18 species, although 12 species were represented by four or fewer animals (Table 3). Initial screening of the available 110 rectal swabs with the pan Flu RT-PCR assay described in Example 1, identified a flat-faced fruit bat (ID PEBT033) (*Artibeus Planirostris*) from Truenococha, as positive for influenza virus. A BLAST search based on the 250 nucleotide sequence of the PB1 RT-PCR amplicon showed that the influenza gene in the PEBT033 bat was most closely related (77% nucleotide identity) to the PB1 genes of the bat influenza viruses described in Example 1, e.g. A/little yellow-shouldered bat/Guatemala/164/2009 (H17N10). The RNA from bat PEBT033 swab sample was analyzed by Sanger and deep sequencing to generate a full-length genomic sequence, and this virus was designated A/flat-faced bat/Peru/033/2010 (A/bat/Peru/10). This confirmed that the Pan-influenza RT-PCR detection assay described in Example 1 can detect novel influenza viruses in a population.

TABLE 3

Detection of influenza A virus and antibody in bats from Peru

| Species | Location (no. captured) | Pan-Flu RT-PCR: No. positive, No. tested | Seropreval; ence: No. positive/No. tested sera (%) |
|---|---|---|---|
| *Artibeus lituratus* | Truenococha (3) | 0, 3 | 3/3 (100%)† |
| *Artibeus obscurus* | Santa Marta (1); Truenococha (9) | 0, 10 | 9/10 (90%)† |
| *Artibeus planirostris* | Santa Marta (1); Truenococha (14) | 1†*, 15 | 13/15 (87%)† |
| *Carollia brevicauda* | Santa Marta (2) | 0, 2 | 1/2 (50%)† |
| *Carollia castanea* | Santa Marta (2) | 0, 2 | 0/2 (0%) |
| *Carollia perspicillata* | Santa Marta (26); Truenococha (4) | 0, 29 | 11/29 (38%)† |
| *Desmodus glaucus* | Truenococha (1) | 0, 1 | 0/1 (0%) |
| *Desmodus rotundus* | Santa Marta (12); Truenococha (6) | 0, 18 | 7/18 (39%)† |
| *Diphylla ecaudata* | Santa Marta (1) | 0, 1 | 0/1 (0%) |
| *Glossophaga soricina* | Santa Marta (1); Truenococha (3) | 0, 2 | 0/2 (0%) |
| *Molossus molossus* | Santa Marta (10) | 0, 10 | 3/10 (30%)† |
| *Myotis* sp. | Santa Marta (6) | 0, 6 | 1/6 (17%)† |
| *Phyllostomus discolor* | Santa Marta (1); Truenococha (1) | 0, 2 | 2/2 (100%)† |
| *Phyllostomus hastatus* | Truenococha (2) | 0, 2 | 2/2 (100%)† |
| *Platyrrhinus recifinus* | Truenococha (1) | 0, 1 | 1/1 (100%)† |
| *Rhinophylla pumilio* | Santa Marta (2) | 0, 2 | 1/2 (50%)† |
| *Stumira* sp. | Santa Marta (2) | 0, 2 | 0/2 (100%) |
| *Vampyressa bidens* | Truenococha (3) | 0, 2 | 1/2 (50%)† |

†influenza A positive samples; *, novel virus

Phylogenetic analysis indicated that all genes of A/bat/Peru/10 were most closely related to those of bat influenza viruses from Guatemala (FIGS. 4A and B). With the notable exception of the HA, the bat virus genes (i) fell as an outgroup to all other known influenza A viruses, and (ii) harbored more genetic diversity than those present in all non-bat (e.g., avian, mammalian) groups combined. In contrast, the bat HA gene sequences represented a distinct lineage within the known diversity of HA genes. The magnitude of the evolutionary distance between the A/bat/Peru/10 HA gene and the A/bat/Guatemala/164/09 virus HA, previously classified as subtype H17, supports its designation as H18, a new distinct HA subtype.

The contrasting phylogenetic position of the bat HA genes relative to the other seven genes is consistent with introduction into bats through reassortment after gene divergence into bat and non-bat lineages. In contrast, phylogeny of the NA gene resembles that of "internal genes" (PB2, PB1, PA, NP, MP, NS) rather than the HA, an intriguing finding given the functional interdependence of these genes in non-bat influenza viruses.

Peruvian bat virus genes formed a strongly supported monophyletic group distinct from Guatemalan bat virus (FIGS. 4A and B). More striking was the extent of the genetic diversity within the four bat viruses. Notably, the divergence between Peruvian and Guatemalan PB2, PB1, PA and NA genes is greater than those among all other homologous influenza genes (FIGS. 4A and B). Considering the limited geographic area and bat species numbers sampled in the Americas, the remarkable divergence between A/bat/Peru/10 and Guatemalan bat viruses suggests that New World bat species may carry a diverse pool of influenza viruses.

Of note, the ratio of non-synonymous and synonymous substitutions per site (dN/dS) was generally lower in New World bats compared to observations in other species, and significantly in the case of PB2, PB1, PA, NP, MP and NS genes (Table 4). Hence, bat influenza viruses are subject to stronger purifying selection than from other animal species, in turn suggestive of longterm evolution and host adaptation. The higher dN/dS values in the HA, NA, and NS genes may be indicative of positive selection for antibody (HA and NA) and innate immunity (NS) escape in these genes (Fitch et al., *Proc. Natl. Acad. Sci. USA* 94:7712-7718, 1997; Fitch et al., *Proc. Natl. Acad. Sci. USA* 88:4270-4274, 1991; Voeten et al., *J. Virol.* 74:6800-6807, 2000).

subtypes (47.8%) (FIG. 5). Despite such divergence, canonical sequence motifs conserved across non-bat subtypes of HA, such as putative disulfides, receptor binding site (RBS), HA0 cleavage sites, coiled-coil heptad repeats and the fusion peptide, were readily identified. The HA proteins from A/bat/Peru/10 and the recently identified H17 from Guatemalan bat share only 62.3% sequence identity. This divergence is greater than the pairwise differences between 12 of the 136 possible pairwise comparisons between all subtypes, supporting the designation of the new HA as representative of subtype H18 (Rohm et al., *Virology* 217:508-516, 1996). The NA-like (NAL) protein of A/bat/Peru/10 has 29.6% identity with all other NA subtypes, correlated with poor residue conservation comprising the canonical catalytic site (FIG. 6), supporting the proposed designation of A/bat/Peru/10 NAL as subtype N11.

To assess the seroprevalence of infection in South American bat populations, panels of sera were analyzed to identify IgG antibodies to recombinant bat influenza H18 HA (rHA) and N11 NAL (rNAL) by indirect ELISA. Specific IgG antibody titers to bat rHA or rNAL (>1:1,000) were detected among 55 of 110 bats (Table 3) from Peru. High titers (>1:16,000) to rHA or rNAL were detected in 11 sera (10%). A high proportion of these 55 bat sera (21 samples) were positive for both rHA and rNAL, whereas 30 were positive for rHA only and 4 positive for rNAL only. As HA is generally immunodominant, absence of antibodies to HA in NAL-seropositive animals suggest that bat viruses with an unknown subtype of HA, in combination with N11, may have infected these animals (Johansson et al., *Proc. Natl. Acad. Sci. USA* 84:6869-6873, 1987). The proportion of seropositive samples was highest among *Artibeus* in Truenococha (25 of 28 tested, positive for rHA or rNA). Five additional bat species also appear to be highly seropositive despite small sample sizes (Table 3).

TABLE 4

| dN/dS ratios | | | | | | | | |
|---|---|---|---|---|---|---|---|---|
| Gene | PB2 | PB1 | PA | HA | NP | NA | MP | NS |
| Bats | 0.008** | 0.008** | 0.009** | 0.033 | 0.011** | 0.075 | 0.012** | 0.076** |
| Others | 0.026 | 0.025 | 0.039 | 0.054 | 0.033 | 0.060 | 0.046 | 0.185 |

**significantly lower in bats than other species

Key structural features of the Peruvian bat influenza virus genome, including RNA transcription and replication promoter elements, open reading frames and mRNA splice signals, and ribosomal frameshift element (PA gene), are nearly identical to recently described Guatemalan bat influenza genomes and likely to serve equivalent functions (Jagger et al., *Science* 337:199-204, 2012; Shi et al., *J. Virol.* 86:12411-12413, 2012). Comparison of the genomes of the two viruses shows nucleotide sequence identity of 48.7-62.3% for genes encoding viral surface proteins and 76.2 to 81.6% for those encoding internal proteins (Table 5).

TABLE 5

Nucleotide sequence identify between A/flat-faced bat/Peru/033/2010 (H18N11) and A/little yellow-shouldered bat/Guatemala/164/2009 (H17N10) genomes

| Gene (A/bat/Peru/10) | % Identity with A/bat/Guat/164/09 |
|---|---|
| PB2 | 76.5 |
| PB1 | 76.2 |
| PA | 78.3 |
| HA | 62.3 |
| NP | 78.9 |
| NA | 48.7 |
| M | 81.6 |
| NS | 78.9 |

Influenza HA and NA proteins are critical for interaction with the host and determining the subtype of influenza type A viruses. Mean pairwise amino acid sequence identity of the HA of A/bat/Peru/10 with Group 1 HA subtypes was 49.1%, comparable to the average identity among all HA The high seroprevalence of bat influenza in bats from the Loreto Department in Peru prompted analysis of 228 serum samples from eight locations in southern Guatemala in 2009-2010. Specific antibodies to bat H17 subtype rHA were detected by ELISA in 86 of the 228 sera from eight bat species (Table 6). Temporal and spatial sampling limitations notwithstanding, the high seroprevalence influenza virus infection in multiple species suggests widespread circulation of influenza A viruses among New World bats.

TABLE 6

Seroprevalence of IgG in Guatemalan bats to H17 rHA by ELISA

| Species | ELISA+ | Tested |
|---|---|---|
| Sampled in 2009 | | |
| *Artibeus jamaicensis* | 9 | 12 |
| *Artibeus lituratus* | 2 | 7 |
| *Carollia perspicillata* | 1 | 3 |
| *Centurio senex* | 0 | 1 |
| *Desmodus rotundus* | 9 | 41 |

TABLE 6-continued Seroprevalence of IgG in Guatemalan bats to H17 rHA by ELISA

| Species | ELISA+ | Tested |
|---|---|---|
| Glossophaga soricina | 2 | 6 |
| Micronicterius nicrotis | 0 | 3 |
| Phyllostomus discolor | 2 | 2 |
| Pteronotus davyi | 0 | 5 |
| Sturnira lilium | 13 | 21 |
| Sturnira ludovici | 0 | 1 |
| Vampyressa pusilla | 0 | 2 |
| Sampled in 2010 | | |
| Artibeus jamaicensis | 8 | 24 |
| Artibeus lituratus | 3 | 5 |
| Artibeus phaeotis | 1 | 1 |
| Artibeus toltecus | 0 | 1 |
| Carollia perspicillata | 2 | 8 |
| Desmodus rotundus | 5 | 26 |
| Eptesicus fuscus | 0 | 2 |
| Glossophaga soricina | 7 | 13 |
| Macrophyllum macrophyllum | 1 | 1 |
| Molossus sinaloae | 0 | 2 |
| Myotis nigricans | 0 | 2 |
| Platyrrhinus helleri | 0 | 10 |
| Sturnira lilium | 21 | 28 |
| Uroderma bilobatum | 0 | 1 |

EXAMPLE 4

Additional Pan-Flu RT-PCR Assay

An additional Pan-Flu RT-PCR assay was developed. Further primers capable of amplifying influenza PB1 were designed. The primer sequences are shown in Table 7. The primers were tested on the panel of 34 influenza viruses shown in Table 2. The primers were also tested with PB1 plasmid DNA from the novel bat influenza viruses described in Examples 1 and 3. RT-PCR was performed as described in Example 2, using the new primers.

TABLE 7

Additional pan-influenza RT-PCR primers

| Primer | Sequence (5' -> 3') | SEQ ID NO: |
|---|---|---|
| Flu-Pan-F2-2 | CCAGTTGGAGGIAATGARAAGAANGC | 9 |
| Flu-Pan-R3-3 | CATTCATTCCATTTIGTRTTRTCNCC | 10 |

I = inosine;
R = purine;
N = degenerate base (mixture of A, C, G, and T)

Figure 7:
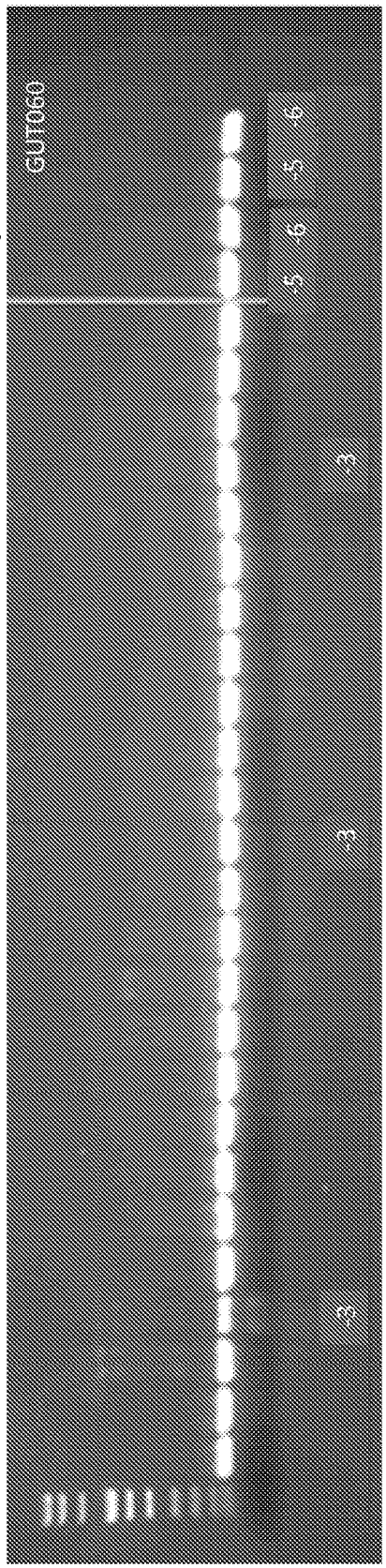
FIG. 7 is a pair of digital images showing amplification of RNAs from 34 different viruses belonging to the genera Influenza virus A, Influenza virus B, and Influenza virus C by one step RT-PCR with the pan-influenza primer pair SEQ ID NOs: 9 and 10. The reference number of each virus (as designated in Table 2) is shown above each sample. Peru033 and GUT060 are bat sample designations. The numbers below the lanes indicate serial dilutions of virus template.
Figure 7:
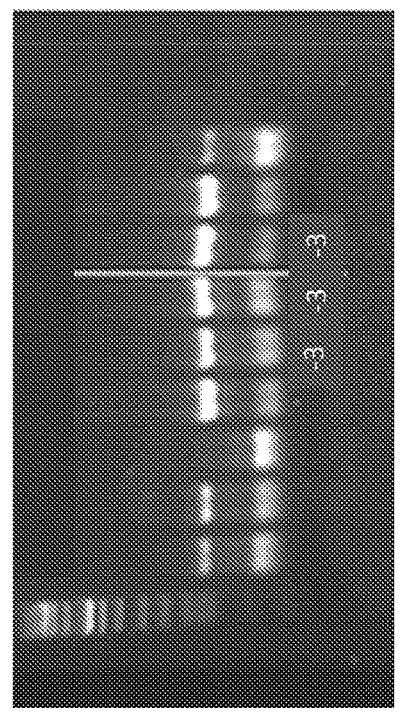

All of the 34 tested influenza reference viruses (representing 25 influenza A (H1-H15), 6 influenza B (both Yamagata and Victoria lineages) and 3 influenza C viruses) were successfully detected by RT-PCR with the pan-influenza primers shown in Table 7 (FIG. 7). The novel bat influenza viruses were also detected with this set of primers (FIG. 7).

EXAMPLE 5

Detection of Influenza Virus

This example describes exemplary methods that can be used to detect influenza virus nucleic acids in a sample from a subject, thereby diagnosing the subject with infection with influenza virus. However, one of ordinary in the art will appreciate that methods that deviate from these specific methods can also be used to successfully detect influenza virus nucleic acids in a sample and determine a diagnosis for the subject.

Clinical samples are obtained from a subject (such as a subject suspected of having an influenza virus infection or a subject for monitoring or surveying presence of influenza virus in a population), such as a nasopharyngeal, oropharyngeal, or bronchial swab, bronchoalveolar lavage, sputum, or oral or rectal swab. Nucleic acids (such as DNA, RNA, or total nucleic acid) are extracted from the sample using routine methods (for example using a commercial kit).

RT-PCR reactions include 2 µM each of forward and reverse primers (SEQ ID NOs: 4 and 5, respectively or SEQ ID NOs: 9 and 10, respectively), 1× buffer with a final concentration of 2.0 mM $MgSO_4$, 0.2 mM (each) deoxynucleoside triphosphates, 20 U of RNase inhibitor, 5 µl total nucleic acid, and 2 µl of SUPERSCRIPT™ III RT/Platinum Taq mix (Invitrogen) or other suitable RT-PCR mix. The reaction mix is incubated for 30 minutes at 50° C., followed by 2 minutes at 94° C., 40 cycles for 15 seconds at 94° C., 30 seconds at 50° C. and 1 minute at 72° C., and a final extension at 72° C. for 7 minutes in an automated thermal cycler. Amplification products are detected, for example by gel or capillary electrophoresis. Presence of an amplification product in a sample indicates presence of influenza virus in the subject.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A method of detecting presence of influenza virus in a sample, comprising:

amplifying from the sample an influenza virus polymerase basic protein 1 (PB1) nucleic acid comprising contacting the sample with a pair of primers capable of hybridizing to an influenza virus PB1 nucleic acid, wherein the pair of primers comprises a forward primer consisting of the nucleic acid sequence of SEQ ID NO: 4 and a reverse primer consisting of the nucleic acid sequence of SEQ ID NO: 5 or a forward primer consisting of the nucleic acid sequence of SEQ ID NO: 9 and a reverse primer consisting of the nucleic acid sequence of SEQ ID NO: 10, to produce an amplified PB1 nucleic acid; and detecting the amplified PB1 nucleic acid, wherein presence of the amplified PB1 nucleic acid indicates presence of influenza virus in the sample.

2. The method of claim 1, wherein the influenza virus comprises an influenza A virus, an influenza B virus, an influenza C virus, or a combination of two or more thereof.

3. The method of claim 1, wherein amplifying the PB1 nucleic acid comprises reverse transcription-polymerase chain reaction (RT-PCR), real-time PCR; quantitative real-time PCR, or real-time reverse transcriptase PCR.

4. The method of claim 1, further comprising contacting the sample with a probe capable of hybridizing to the amplified PB1 nucleic acid.

5. The method of claim 4, wherein the probe is detectably labeled.

6. The method of claim 1, further comprising sequencing the amplified PB1 nucleic acid.

7. The method of claim 6, further comprising comparing the sequence of the amplified PB1 nucleic acid to one or more known influenza virus PB1 nucleic acid sequences to determine the influenza virus subtype present in the sample.

\* \* \* \* \*

SEQUENCE LISTING

<160> NUMBER OF SEQ ID NOS: 10

<210> SEQ ID NO 1
<211> LENGTH: 2274
<212> TYPE: DNA
<213> ORGANISM: Influenza A virus

<400> SEQUENCE: 1

```
atgaatgtca atccgactct acttttccta aaggttccag tgcaaaatgc cataagcacc      60
acattccctt atactggaga tcctccatac agccatggaa caggaacagg atacaccatg     120
gacacagtca acagaacaca ccaatattca gaaaaaggga aatggactac aaacacagag     180
```

| | |
|---|---|
| actgggcac cccagctcaa cccgattgat ggaccactac ctgaagataa tgaaccgagt | 240 |
| ggatatgcac aaacagactg tgtcctggaa gccatggctt tccttgaaga atcccaccca | 300 |
| gggatatttg agaattcatg ccttgagaca atggagattg ccaacaaac aagggtggat | 360 |
| aaactaactc aaggtcgcca gacttatgat tggacattaa acagaaatca accggctgca | 420 |
| actgcattgg ccaacaccat agaagttttt agatcaaatg gtctaacagc taatgagtca | 480 |
| ggaaggctga tagatttcct aaaggatgta atggaatcaa tggataaaga ggaaatagag | 540 |
| ataacaacac actttcaaag gaaaaggaga gtaagagaca catgaccaa gaagatggtc | 600 |
| acacaaagaa caatagggaa gaaaaaacaa agagtgaata agagaagtta tctaataaga | 660 |
| gcactgacat tgaatacgat gaccaaagat gcagaaagag gcaaattaaa aaggagggcc | 720 |
| atcgcaacac tgggatgca atcagagggg ttcgtgtact tgttgagat tttagctaga | 780 |
| agcatttgcg aaaagcttga acagtccgga ctcccagtag ggggcaatga aaagaaagcc | 840 |
| aaattggcaa atgttgtgag aaagatgatg accaattcac aagacacaga gctttctttc | 900 |
| acaatcactg agacaacac taaatggaat gaaaaccaaa atcctcgaat gttcctggcg | 960 |
| atgattactt acatcaccag aaatcaaccc gagtggttca gaaacatact gagtatggca | 1020 |
| ccgataatgt tctcaaacaa aatggcaaga ctaggaaaag ggtacatgtt cgagagtaaa | 1080 |
| agaatgaagc tccgaacaca gataccagca gaaatgctag caagcattga cctgaagtat | 1140 |
| ttcaatgaat caacaaggaa gaaaattgag aaaataaggc ctctcctaat aaatggcaca | 1200 |
| gcatcattga gtcctggaat gatgatgggc atgttcaata tgctaagtac ggttttggga | 1260 |
| gtctcaatac taaatcttgg acaaagaaa tacaccagga caacatactg gtgggatgga | 1320 |
| ctccaatctt ccgacgattt tgccctcata gtaaattcac caaatcatga gggaatacaa | 1380 |
| gcaggagtgg atagattcta caggacatgc aagttagtag ggatcaacat gagcaaaaag | 1440 |
| aagtcctata taaataaaac tgggacattt gaattcacaa gctttttta tcgctatggg | 1500 |
| tttgtagcta atttagcat ggaactgccc agttttggag tgtctggaat aaacgaatca | 1560 |
| gctgatatga gtattgggat aacagtgata agaacaaca tgataaataa tgatcttgga | 1620 |
| cctgcaacag cccagatggc ccttcagtta ttcatcaaag actacagata cacatataga | 1680 |
| tgtcatagag gggacacaca aattcagacg agaagatcat tcgagctaaa aagcctgtgg | 1740 |
| gatcaaaccc aatcgaaggc aggattatta gtatctgatg gaggaccgaa tttatacaat | 1800 |
| atccggaatc ttcacattcc tgaagtctgc ttaaaatggg aactaatgga tgaggattat | 1860 |
| aggggtagac tttgtaatcc tctgaacccc tttgtcagcc acaaagagat tgattctgtc | 1920 |
| aacagtgctg tggtgatgcc agcccatggt ccagccaaaa gtatggaata tgatgccgtt | 1980 |
| gcaaccacac actcctggat tcccaagaga accgctcta ttctcaacac aagccaaagg | 2040 |
| ggaattcttg aagatgaaca gatgtaccag aagtgttgta acctgttcga aaatttttc | 2100 |
| cctagtagtt catacaggag accggttgga atttctagca tggtgaggc catggtgtct | 2160 |
| agggcccgga ttgatgccag gattgatttc gagtctggac ggattaagaa agaagagttc | 2220 |
| tctgagatca tgaagatctg ttccaccatt gaagaactca gacggcaaaa gtaa | 2274 |

<210> SEQ ID NO 2
<211> LENGTH: 2368
<212> TYPE: DNA
<213> ORGANISM: Influenza B virus

<400> SEQUENCE: 2

```
agcagaagcg gagctttaag atgaatataa atccatattt tcttttcata gatgtaccta        60
tacaggcagc aatttcaaca acattcccat acaccggtgt tcccccttat tctcatggaa       120
cgggaacagg ctacacaata gacaccgtga ttagaacaca cgagtactca aacaagggaa       180
aacaatacat ttctgatgtt acaggatgtg taatggtaga tccaacaaat gggccattac       240
ccgaagacaa tgaaccgagt gcctatgcac aattggattg tgttctggag ctttggata        300
gaatggatga gaacatcca ggtctgtttc aagcagggtc acagaatgcc atggaggcac        360
taatggtcac aacagtggac aaattgactc aggggagaca gacctttgat tggacggtgt       420
gtagaaacca acctgctgca acggcactga acacaacaat aacctctttt aggttgaatg       480
atttaaatgg agccgacaag ggtggattag tgcccttttg ccaagatatc attgattcat       540
tagacaaacc tgaaatgatt ttcttcacag taaagaatat aaagaaaaaa ttgcctgcta       600
aaaacagaaa gggtttcctt ataaaaagaa tacctatgaa ggtaaaagac agaataacaa       660
gagtggaata catcaaaaga gcattatcat taaacacaat gactaaagat gctgaaagag       720
gcaaactaaa aagaagagca attgccaccg ctgggataca aatcagagga tttgtattag       780
tagttgaaaa cttggctaaa aatatctgtg aaaatctaga gcaaagtggt ttacccgtag       840
gtggaaacga aaagaaggcc aaactatcaa atgcagtggc taaaatgctc agtaattgtc       900
caccaggagg gatcagtatg actgtgacag gagacaatac taaatggaat gaatgcttaa       960
atccaagaat cttttttggct atgactgaaa gaataaccag agacagccca atttggttcc      1020
gggattttg tagtatagca ccggtcttgt tctccaataa aatagctaga ttgggaaaag        1080
ggttcatgat aacaagtaaa acaaaaagac taaaagctca aatccttgt cccgatctgt        1140
ttaatatacc attagaaaga tataatgaag aaacaagggc aaaactgaaa aagctaaaac      1200
ctttcttcaa tgaagaagga acggcatctc tttcgccagg aatgatgatg ggaatgttta      1260
atatgctatc tacagtatta ggagtagccg cactagggat aaaaaacatt ggaaacaaag      1320
aatacttatg ggatggactg cagtcttcgg atgattttgc tctgtttgtt aatgcaaaag      1380
atgaagagac atgtatggaa ggaataaacg attttaccg aacatgtaag ctattgggaa       1440
taaacatgag caaaaagaaa agttactgta atgaaactgg gatgtttgaa tttaccagca      1500
tgttttacag agatggattt gtatctaatt ttgcaatgga actcccttca tttggagtcg      1560
ctggagtgaa tgaatcagca gacatggcaa taggaatgac aataataaag aacaatatga      1620
tcaacaatgg gatgggccca gcaacggcac aaacagccat acaattattc atagctgact      1680
atagatacac ctacaaatgc cacaggggag attccaaagt ggaagggaag agaatgaaaa      1740
ttataaagga gctatgggaa acactaaag gaagagatgg tctattagta gcagatggtg        1800
ggcctaatct ttcaatttg agaaacctgc atattccaga ataatatta aatacaaca          1860
taatggaccc tgagtacaaa ggacggttac tgcatcctca aaatcccttt gtaggacatt      1920
tgtctattga gggtatcaaa gaagcagata taacacctgc acatggccca ataaagaaaa      1980
tggactacga tgcggtatct ggaactcata gttggagaac caaaggaac agatctatac       2040
taaacactga tcagaggaac atgattcttg aggaacaatg ctacgctaag tgttgcaacc      2100
tttttgaggc ttgcttaac agtgcgtcat acagaaaacc agtaggccag cacagcatgc       2160
ttgaagctat ggcccacaga ttaagaatgg atgcacgact ggactatgag tcaggaagga      2220
tgtcaaaaga ggatttcgaa aaagcaatgg ctcaccttgg tgagattggg tacatgtaag      2280
ctccggaaat gtctatgggg ttattggtca tcgttgaata catgcggtgc acaaatgatt      2340
aaaatgaaaa aaggctcgtg tttctact                                         2368
```

<210> SEQ ID NO 3
<211> LENGTH: 2363
<212> TYPE: DNA
<213> ORGANISM: Influenza C virus

<400> SEQUENCE: 3

| | | | | | |
|---|---|---|---|---|---|
| agcagaagca | gaggattatg | gaaatcaacc | catatttgat | gtttctaaac | aacgacgtta | 60 |
| catcgctgat | atcaacaaca | taccccctata | cagggccacc | tccaatgtca | catggatcat | 120 |
| caaccaaata | cactttggaa | actattaaaa | gaacatatga | ctactcaaga | acatcagttg | 180 |
| aaaaaacatc | gaaggttttc | aatataccaa | gaagaaagtt | ttgcaattgt | cttgaagaca | 240 |
| aagatgattt | ggtaaaacca | acaggaaacg | ttgatatcag | ttccttgttg | ggccttgcag | 300 |
| agatgatgga | gaaagaatg | ggagaaggat | tttttaagca | ttgtgtaatg | gaggcagaaa | 360 |
| cagaaatact | aaaatgcac | ttctctagac | ttacggaagg | aagacaaaca | tatgattgga | 420 |
| cttctgaaag | aaacatgcca | gcggccactg | ctttgcaact | gacagttgat | gccataaaag | 480 |
| aaacagaagg | accatttaaa | gggacaacaa | tgcttgaata | ttgcaataaa | atgatagaaa | 540 |
| tgcttgattg | gaaagaagtt | aaattcagaa | aagtcaaaac | aatggtgaga | agggagaaag | 600 |
| ataaaagaag | tgggaaggag | ataaaaaacta | aagtacctgt | aatgggaatt | gactcaatta | 660 |
| aacatgatga | gttttaatt | agagcattaa | ctattaatac | catggccaaa | gatggggaaa | 720 |
| gagggaaatt | gcaaagaaga | gcaattgcaa | cacccggtat | gatagtaaga | ccattttcaa | 780 |
| aaattgttga | aactgtagca | cagaaaatat | gtgagaaatt | gaagaaaagc | ggtctacctg | 840 |
| ttggtggtaa | tgagaagaaa | gcaaaactta | agaccactgt | tacttctctc | aatgccagga | 900 |
| tgaacagtga | tcagtttgca | gttaatataa | ctggagacaa | tagtaaatgg | aatgaatgcc | 960 |
| aacaacctga | ggcttattta | gcacttttgg | cttacatcac | caaagactcc | tctgatttaa | 1020 |
| tgaaagactt | atgcagtgtt | gctccagtac | ttttctgtaa | taagtttgtg | aaacttggac | 1080 |
| aaggaataag | actttcaaat | aaaagaaaaa | caaaggaagt | cataataaaa | gctgagaaaa | 1140 |
| tgggaaaata | caagaatcta | atgagagaag | aatataaaaa | ccttttgaa | cccttagaaa | 1200 |
| aatatattca | gaaggatgtc | tgtttttac | ctggaggaat | gcttatggga | atgttcaaca | 1260 |
| tgctgtcaac | agttcttgga | gtgagtacat | tatgttatat | ggatgaagaa | ctaaaagcca | 1320 |
| aaggatgttt | ttggactgga | ctccaatctt | ctgatgactt | tgttcttttt | gcagttgctt | 1380 |
| caaactggtc | aaatatacat | tggacaataa | gacggtttaa | tgctgtatgc | aagttaattg | 1440 |
| gtataaacat | gtctcttgaa | aaatcgtatg | gttctctccc | agaactcttt | gaatttacaa | 1500 |
| gtatgttctt | tgatggagaa | tttgtgtcca | atcttgctat | ggaattgcca | gctttcacta | 1560 |
| ctgcaggagt | taatgaagga | gttgatttta | cagctgcaat | gtcaattatt | aagacaaata | 1620 |
| tgataaataa | cagcttatca | ccttctactg | ctttaatggc | cttaaggata | tgtctccaag | 1680 |
| aatttagagc | gacttataga | gtccatcctt | gggattcaaa | agtgaaaggt | gggagaatga | 1740 |
| aaataataaa | tgagttcata | aagaccatag | aaagtaaaga | tggattatta | attgctgatg | 1800 |
| gtgggaaact | gatgaacaac | attagcaccc | ttcatattcc | tgaggaagta | ctgaagtttg | 1860 |
| aaaaaatgga | tgaacaatat | agaaatagggg | tattcaaccc | caaaaatccc | tttactaact | 1920 |
| ttgacaaaaac | tatcgatata | tttagagcac | atggcccaat | aagggttgaa | gaaaatgaag | 1980 |
| cagtagtttc | aactcatagc | ttcagaacca | gagcaaacag | aacccctattg | aatacagata | 2040 |
| tgagagcaat | gatggcagaa | gagaaaagat | atcaaatggt | ttgcgacata | tttaaaagcg | 2100 |

```
tgtttgaatc agcggacata aatcctccaa ttggggctat gagcattgga gaggccatag    2160
aagagaaact attagagaga gctaaaatga aaagagacat tggggcaata gaagattcag    2220
aatatgaaga aataaaagac attataaggg atgcaaagaa agctagaatt gaaagtagat    2280
gaggaggggc tgttaaaccc tttcctccta cttgcacata tttttgttat tccattaaat    2340
gaaaaaatcc tcttgctact gct                                            2363

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is a, c, g, and t

<400> SEQUENCE: 4
acnggagaca anacnaaatg gaatga                                          26

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is a, c, g, and t
<220> FEATURE:
<221> NAME/KEY: misc_feature
<222> LOCATION: (24)..(24)
<223> OTHER INFORMATION: n is a, c, g, and t

<400> SEQUENCE: 5
actgttgaca gcatnttnaa catnccc                                         27

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
ccattatgag ggtccccact                                                 20

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 7
```

```
ggatgtgctc gttgatgca                                              19

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 8
tcccagctgc tccagctctt ctt                                         23

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (24)..(24)
<223> OTHER INFORMATION: n is a, c, g, and t

<400> SEQUENCE: 9
ccagttggag gnaatgaraa gaangc                                      26

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (24)..(24)
<223> OTHER INFORMATION: n is a, c, t, and g

<400> SEQUENCE: 10
cattcattcc atttngtrtt rtcncc                                      26
```